United States Patent [19]

Watson et al.

[11] Patent Number: 5,298,480
[45] Date of Patent: Mar. 29, 1994

[54] HERBICIDAL SULFONYLUREA DERIVATIVES

[75] Inventors: Keith Watson, Blackburn; Wayne Best, Avondale Heights, both of Australia

[73] Assignee: ICI Australia Operations Proprietary Limited, Melbourne, Australia

[21] Appl. No.: 701,166

[22] Filed: May 17, 1991

[30] Foreign Application Priority Data

May 17, 1990 [AU] Australia ............................. PK 0181

[51] Int. Cl.$^5$ ..................... C07D 403/12; A01N 43/66
[52] U.S. Cl. .................................. 504/213; 544/212; 544/207; 544/209
[58] Field of Search ............... 544/212, 207, 209; 71/93; 504/213

[56] References Cited

U.S. PATENT DOCUMENTS

| | | | |
|---|---|---|---|
| 4,612,037 | 9/1986 | Bohner et al. | 71/92 |
| 4,681,620 | 7/1987 | Bohner et al. | 71/93 |
| 4,684,730 | 8/1987 | Bohner et al. | 544/408 |
| 4,707,551 | 11/1987 | Bohner et al. | 544/408 |
| 4,792,608 | 12/1988 | Bohner et al. | 544/319 |
| 4,804,757 | 2/1989 | Bohner et al. | 544/319 |

FOREIGN PATENT DOCUMENTS 0096004 12/1983 European Pat. Off. .

*Primary Examiner*—John M. Ford
*Attorney, Agent, or Firm*—Cushman, Darby & Cushman

[57] ABSTRACT

The invention embraces compounds of formula

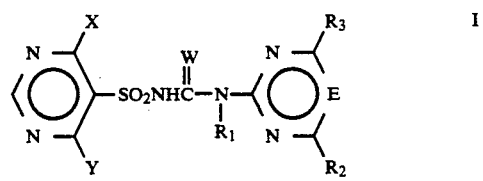

and salts thereof, wherein:

X and Y are independently selected from various optionally substituted alkoxy, alkenyloxy, alkynyoxy and phenoxy groups;
W is oxygen or sulfur;
$R_1$ is hydrogen or alkyl;
E is CH or N;
$R_2$ and $R_3$ are independently selected from various halo, alkyl, alkoxy and amino substituents.

The compounds of the invention show herbicidal properties particularly for the control of broad leaf plants in grass crops such as wheat. In further embodiments the invention provides processes for the preparation of compounds I, intermediates useful in the preparation of compounds of formula I, compositions containing as active ingredient a compound of formula I and herbicidal and plant growth regulating processes utilizing compounds of formula I.

7 Claims, No Drawings

HERBICIDAL SULFONYLUREA DERIVATIVES

This invention relates to organic compounds having biological activity and in particular to organic compounds having herbicidal properties and plant growth regulating properties, to processes for the preparation of such compounds, to intermediates useful in the preparation of such compounds and to herbicidal compositions and processes utilizing such compounds.

The use of certain sulfonylurea derivatives as herbicides is known in the art. Thus, for example, the "Pesticide Manual" (C R Worthing Editor, The British Crop Protection Council, 7th Edition 1983) describes the sulfonylurea derivative known commercially as chlorsulfuron [1-(2-chlorophenylsulfonyl)-3-(4-methoxy-6-methyl-1,3,5-triazin-2-yl) urea] and its use as a broadleaf weed herbicide in cereals. This compound is described in Australian Patent No. 510,056.

Whilst chlorsulfuron has proved to be a useful herbicide for the control of many broadleaf weeds in cereal crops, the compound does have shortcomings such as low activity on many grass weeds and a high soil persistence.

European Patent Application 0 096 004 (published November 1983) discloses herbicidal sulfonylureas of the general formula $$QSO_2NHCN-Het$$
$$\overset{\overset{Z}{\|}}{\underset{R_1}{|}}$$

wherein $R_1$ is hydrogen or $C_1$–$C_5$ alkyl;

Z is oxygen or sulfur;

Het is a pyrimidyl or triazinyl ring; and Q is an unsubstituted or substituted 6-membered heterocyclic radical containing 2 or 3 nitrogen atoms and bound through a carbon atom.

It has now been found that a small group of 5-pyrimidyl sulfonylurea derivatives which have not previously been disclosed and which are not readily accessible by established methods exhibit particularly useful herbicidal activity. Accordingly the present invention relates to novel 5-pyrimidylsulfonyl-N-pyrimidimyl- and N-triazinylureas with herbicidal and growth regulating properties, to the preparation thereof, to compositions containing them, and to the use thereof for controlling weeds, in particular selectively, in crops of useful plants or for regulating and inhibiting plant growth.

The invention provides compounds of the formula I wherein

X and Y are independently selected from $C_1$–$C_4$ alkoxy, $C_1$–$C_4$ haloalkoxy, $C_3$–$C_4$ alkenyloxy, $C_3$–$C_4$ haloalkenyloxy, $C_3$$C_4$ alkynyloxy and $C_1$–$C_3$ alkoxy ($C_1$–$C_3$alkoxy), and phenoxy or substituted phenoxy where the substituents are selected from halogen, methyl, trifluoromethyl, nitro, or methoxy, with the proviso that X and Y cannot both be methoxy W is oxygen or sulfur;

E is a methine group or nitrogen;

$R_1$ is hydrogen or $C_1$–$C_4$ alkyl;

$R_2$ is methyl, methoxy, ethoxy, halogen, trifluoromethyl or difluoromethoxy;

$R_3$ is hydrogen, methyl, ethyl, methoxy, ethoxy, dimethoxymethyl, methoxymethyl, amino, methylamino, dimethylamino, trifluoromethyl, methylthio, allyloxy, ethoxymethoxy, 2,2,2-trifluoroethoxy or difluoromethoxy.

The invention also includes the salts which the compounds of formula I are able to form with amines, alkali metal bases and alkaline earth metal bases, or with quaternary ammonium bases.

In the definitions given above, the term "alkyl" used either alone or in compound words such as "alkoxy" or "haloalkyl" denotes straight chain or branched alkyl, e.g., methyl, ethyl, n-propyl, isopropyl or the different butyl isomers.

Preferred compounds of the invention include those compounds of formula I in which: X and Y are selected from $C_1$ to $C_4$ alkoxy, $C_1$ to $C_4$ haloalkoxy, $C_3$ to $C_4$ alkenyloxy, $C_3$ to $C_4$ haloalkenyloxy, $C_3$ to $C_4$ alkynyloxy and $C_1$ to $C_3$ alkoxy ($C_1$ to $C_3$ alkoxy) provided X and Y are not both methoxy; E and W are as hereinbefore defined; $R_1$ is hydrogen or $C_1$ to $C_4$ alkyl; $R_2$ is methyl, methoxy, ethoxy, halogen, trifluoromethyl or difluoromethoxy; $R_3$ is hydrogen, methyl, ethyl, methoxy, ethoxy, methoxymethyl, amino, methylamino, dimethylamino, methylthio, allyloxy, 2,2,2-trifluoroethoxy or difluoroethoxy.

More preferred compounds of the invention include those compounds of formula I in which:

X and Y are selected from methoxy, ethoxy, propoxy, isopropoxy, butoxy, difluoromethoxy, 2,2,2-trifluoroethoxy, 2,2,2-trichloroethoxy, allyloxy, propargyloxy and methoxyethoxy provided X and Y are not both methoxy; W is oxygen; E is as hereinbefore defined; $R_1$ is hydrogen or methyl; $R_2$ is methyl, methoxy, ethoxy, halogen, trifluoromethyl or difluoromethoxy; $R_3$ is hydrogen, methyl, ethyl, methoxy, ethoxy, methoxymethyl, amino, methylamino, dimethylamino, methylthio, allyloxy, 2,2,2-trifluoroethoxy or difluoromethoxy.

Preferred values for X and Y include ethoxy, propoxy, isopropoxy, n-butoxy, difluoromethoxy, 2,2,2-trifluoroethoxy, 2,2,2-trichloroethoxy, allyloxy and propargyloxy and particularly preferred values include ethoxy, propoxy, isopropoxy, difluoromethoxy, 2,2,2-trifluoroethoxy and allyloxy.

Preferred values for $R_2$ and $R_3$ include methyl, methoxy, chloro and difluoromethoxy and particularly preferred values include methyl, methoxy and chloro.

Particularly preferred individual compounds include: N-[(4-methoxy-6-methyl-1,3,5-triazin-2-yl) aminocarbonyl]-4,6-diethoxypyrimidine-5-sulfonamide, N-[(4-methoxy-6-methyl-1,3,5-triazin-2-yl) aminocarbonyl]-4,6-bis(2,2,2-trifluoroethoxy) pyrimidine-5-sulfonamide and N-[(4-methoxy-6-methyl-1,3,5-triazin-2-yl)aminocarbonyl]-4-ethoxy-6-(2,2,2-trifluoroethoxy)pyrimidine-5-sulfonamide.

Specific examples of the compounds of the invention include the compounds listed in Table I.

TABLE 1

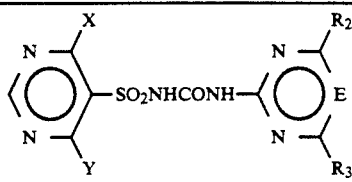

| Compound No. | X | Y | $R_2$ | $R_3$ | E |
|---|---|---|---|---|---|
| 1 | $C_2H_5O$ | $C_2H_5O$ | $CH_3O$ | $CH_3NH$ | CH |
| 2 | $C_2H_5O$ | $C_2H_5O$ | $CH_3O$ | $CH_3O$ | CH |
| 3 | $C_2H_5O$ | $C_2H_5O$ | $CH_3O$ | $CH_3$ | CH |
| 4 | $C_2H_5O$ | $C_2H_5O$ | $CH_3O$ | $CH_3$ | N |
| 5 | $C_2H_5O$ | $C_2H_5O$ | Cl | $CH_3O$ | CH |
| 6 | $C_2H_5O$ | $C_2H_5O$ | $CH_3$ | $CH_3$ | CH |
| 7 | $C_2H_5O$ | $C_2H_5O$ | $CHF_2O$ | $CHF_2O$ | CH |
| 8 | $C_2H_5O$ | $C_2H_5O$ | $CH_3O$ | $CH_3O$ | N |
| 9 | $CF_3CH_2O$ | $CF_3CH_2O$ | $CH_3O$ | $CH_3O$ | CH |
| 10 | $CF_3CH_2O$ | $CF_3CH_2O$ | $CH_3O$ | $CH_3$ | CH |
| 11 | $CF_3CH_2O$ | $CF_3CH_2O$ | $CH_3O$ | $CH_3$ | N |
| 12 | $CF_3CH_2O$ | $CF_3CH_2O$ | Cl | $CH_3O$ | CH |
| 13 | $CF_3CH_2O$ | $CF_3CH_2O$ | $CH_3$ | $CH_3$ | CH |
| 14 | $CF_3CH_2O$ | $CF_3CH_2O$ | $CHF_2O$ | $CHF_2O$ | CH |
| 15 | $CF_3CH_2O$ | $CF_3CH_2O$ | $CH_3O$ | $CH_3O$ | N |
| 16 | $C_2H_5O$ | $CF_3CH_2O$ | $CH_3O$ | $CH_3O$ | CH |
| 17 | $C_2H_5O$ | $CF_3CH_2O$ | $CH_3O$ | $CH_3$ | CH |
| 18 | $C_2H_5O$ | $CF_3CH_2O$ | $CH_3O$ | $CH_3$ | N |
| 19 | $C_2H_5O$ | $CF_3CH_2O$ | Cl | $CH_3O$ | CH |
| 20 | $C_2H_5O$ | $CF_3CH_2O$ | $CH_3$ | $CH_3$ | CH |
| 21 | $C_2H_5O$ | $CF_3CH_2O$ | $CHF_2O$ | $CHF_2O$ | CH |
| 22 | $C_2H_5O$ | $CF_3CH_2O$ | $CH_3O$ | $CH_3O$ | N |
| 23 | $CH_3OCH_2CH_2O$ | $CH_3OCH_2CH_2O$ | $CH_3O$ | $CH_3O$ | CH |
| 24 | $CH_3OCH_2CH_2O$ | $CH_3OCH_2CH_2O$ | $CH_3O$ | $CH_3$ | CH |
| 25 | $CH_3OCH_2CH_2O$ | $CH_3OCH_2CH_2O$ | $CH_3O$ | $CH_3$ | N |
| 26 | $CH_3OCH_2CH_2O$ | $CH_3OCH_2CH_2O$ | Cl | $CH_3O$ | CH |
| 27 | $CHF_2O$ | $CHF_2O$ | $CH_3O$ | $CH_3O$ | CH |
| 28 | $CHF_2O$ | $CHF_2O$ | $CH_3O$ | $CH_3$ | CH |
| 29 | $CHF_2O$ | $CHF_2O$ | $CH_3O$ | $CH_3$ | N |
| 30 | $CHF_2O$ | $CHF_2O$ | Cl | $CH_3O$ | CH |
| 31 | $CHF_2O$ | $CHF_2O$ | $CH_3$ | $CH_3$ | CH |
| 32 | $CHF_2O$ | $CHF_2O$ | $CHF_2O$ | $CHF_2O$ | CH |
| 33 | $CHF_2O$ | $CHF_2O$ | $CH_3O$ | $CH_3O$ | N |
| 34 | $ClCH_2CH_2O$ | $ClCH_2CH_2O$ | $CH_3O$ | $CH_3O$ | CH |
| 35 | $ClCH_2CH_2O$ | $ClCH_2CH_2O$ | $CH_3O$ | $CH_3$ | CH |
| 36 | $ClCH_2CH_2O$ | $ClCH_2CH_2O$ | $CH_3O$ | $CH_3$ | N |
| 37 | $ClCH_2CH_2O$ | $ClCH_2CH_2O$ | Cl | $CH_3O$ | CH |
| 38 | $CH_3O$ | $C_2H_5O$ | $CH_3O$ | $CH_3O$ | CH |
| 39 | $CH_3O$ | $C_2H_5O$ | $CH_3O$ | $CH_3$ | CH |
| 40 | $CH_3O$ | $C_2H_5O$ | $CH_3O$ | $CH_3$ | N |
| 41 | $CH_3O$ | $C_2H_5O$ | Cl | $CH_3O$ | CH |
| 42 | $CH_3O$ | $CF_3CH_2O$ | $CH_3O$ | $CH_3O$ | CH |
| 43 | $CH_3O$ | $CF_3CH_2O$ | $CH_3O$ | $CH_3$ | CH |
| 44 | $CH_3O$ | $CF_3CH_2O$ | $CH_3O$ | $CH_3$ | N |
| 45 | $CH_3O$ | $CF_3CH_2O$ | Cl | $CH_3O$ | CH |
| 46 | $CH_3O$ | $CHF_2O$ | $CH_3O$ | $CH_3O$ | CH |
| 47 | $CH_3O$ | $CHF_2O$ | $CH_3O$ | $CH_3$ | CH |
| 48 | $CH_3O$ | $CHF_2O$ | $CH_3O$ | $CH_3$ | N |
| 49 | $CH_3O$ | $CHF_2O$ | Cl | $CH_3O$ | CH |
| 50 | $CH_3O$ | $CH_3OCH_2CH_2O$ | $CH_3O$ | $CH_3O$ | CH |
| 51 | $CH_3O$ | $CH_3OCH_2CH_2O$ | $CH_3O$ | $CH_3$ | CH |
| 52 | $CH_3O$ | $CH_3OCH_2CH_2O$ | $CH_3O$ | $CH_3$ | N |
| 53 | $CH_3O$ | $CH_3OCH_2CH_2O$ | Cl | $CH_3O$ | CH |
| 54 | $CH_3O$ | $n\text{-}C_3H_7O$ | $CH_3O$ | $CH_3O$ | CH |
| 55 | $CH_3O$ | $n\text{-}C_3H_7O$ | $CH_3O$ | $CH_3$ | CH |
| 56 | $CH_3O$ | $n\text{-}C_3H_7O$ | $CH_3O$ | $CH_3$ | N |
| 57 | $CH_3O$ | $n\text{-}C_3H_7O$ | Cl | $CH_3O$ | CH |
| 58 | $CH_3O$ | $ClCH_2CH_2O$ | $CH_3O$ | $CH_3O$ | CH |
| 59 | $CH_3O$ | $ClCH_2CH_2O$ | $CH_3O$ | $CH_3$ | CH |
| 60 | $CH_3O$ | $ClCH_2CH_2O$ | $CH_3O$ | $CH_3$ | N |
| 61 | $CH_3O$ | $ClCH_2CH_2O$ | Cl | $CH_3O$ | CH |
| 62 | $CH_3O$ | $i\text{-}C_3H_7O$ | $CH_3O$ | $CH_3O$ | CH |
| 63 | $CH_3O$ | $i\text{-}C_3H_7O$ | $CH_3O$ | $CH_3$ | CH |
| 64 | $CH_3O$ | $i\text{-}C_3H_7O$ | $CH_3O$ | $CH_3$ | N |
| 65 | $CH_3O$ | $i\text{-}C_3H_7O$ | Cl | $CH_3O$ | CH |
| 66 | $CH_3O$ | $CH_2=CHCH_2O$ | $CH_3O$ | $CH_3O$ | CH |
| 67 | $CH_3O$ | $CH_2=CHCH_2O$ | $CH_3O$ | $CH_3$ | CH |
| 68 | $CH_3O$ | $CH_2=CHCH_2O$ | $CH_3O$ | $CH_3$ | N |
| 69 | $CH_3O$ | $CH_2=CHCH_2O$ | Cl | $CH_3O$ | CH |
| 70 | $CH_3O$ | $CH{\equiv}CCH_2O$ | $CH_3O$ | $CH_3O$ | CH |

TABLE 1-continued

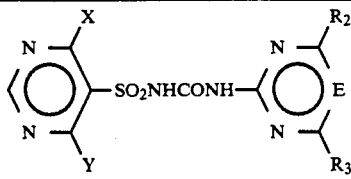

| Compound No. | X | Y | R₂ | R₃ | E |
|---|---|---|---|---|---|
| 71 | CH₃O | CH≡CCH₂O | CH₃O | CH₃ | CH |
| 72 | CH₃O | CH≡CCH₂O | CH₃O | CH₃ | N |
| 73 | CH₃O | CH≡CCH₂O | Cl | CH₃O | CH |
| 74 | C₂H₅O | CH₃OCH₂CH₂O | CH₃O | CH₃O | CH |
| 75 | C₂H₅O | CH₃OCH₂CH₂O | CH₃O | CH₃ | N |
| 76 | CF₃CH₂O | CH₃OCH₂CH₂O | CH₃O | CH₃O | CH |
| 77 | CF₃CH₂O | CH₃OCH₂CH₂O | CH₃O | CH₃ | N |
| 78 | i-C₃H₇O | i-C₃H₇O | CH₃O | CH₃O | CH |
| 79 | i-C₃H₇O | i-C₃H₇O | CH₃O | CH₃ | N |
| 80 | n-C₃H₇O | n-C₃H₇O | CH₃O | CH₃O | CH |
| 81 | n-C₃H₇O | n-C₃H₇O | CH₃O | CH₃ | N |
| 82 | i-C₃H₇O | C₂H₅O | CH₃O | CH₃O | CH |
| 83 | i-C₃H₇O | C₂H₅O | CH₃O | CH₃ | N |
| 84 | C₂H₅O | n-C₃H₇O | CH₃O | CH₃O | CH |
| 85 | C₂H₅O | n-C₃H₇O | CH₃O | CH₃ | N |
| 86 | C₂H₅O | (CF₃)₂CHO | CH₃O | CH₃O | CH |
| 87 | C₂H₅O | (CF₃)₂CHO | CH₃O | CH₃ | N |
| 88 | C₂H₅O | n-C₄H₉O | CH₃O | CH₃O | CH |
| 89 | C₂H₅O | n-C₄H₉O | CH₃O | CH₃ | N |
| 90 | C₂H₅O | C₆H₅O | CH₃O | CH₃O | CH |
| 91 | C₂H₅O | C₆H₅O | CH₃O | CH₃ | N |
| 92 | C₂H₅O | CCl₃CH₂O | CH₃O | CH₃O | CH |
| 93 | C₂H₅O | CCl₃CH₂O | CH₃O | CH₃ | N |
| 94 | C₂H₅O | 4-NO₂C₆H₄O | CH₃O | CH₃O | CH |
| 95 | C₂H₅O | 4-NO₂C₆H₄O | CH₃O | CH₃ | N |
| 96 | C₂H₅O | 2,4-Cl₂C₆H₃O | CH₃O | CH₃O | CH |
| 97 | C₂H₅O | 2,4-Cl₂C₆H₃O | CH₃O | CH₃ | N |
| 98 | CCl₃CH₂O | CCl₃CH₂O | CH₃O | CH₃O | CH |
| 99 | CCl₃CH₂O | CCl₃CH₂O | CH₃O | CH₃ | N |
| 100 | CF₃CF₂CH₂O | CF₃CF₂CH₂O | CH₃O | CH₃O | CH |
| 101 | CF₃CF₂CH₂O | CF₃CF₂CH₂O | CH₃O | CH₃ | N |
| 102 | CH₂=CHCH₂O | CH₂=CHCH₂O | CH₃O | CH₃O | CH |
| 103 | CH₂=CHCH₂O | CH₂=CHCH₂O | CH₃O | CH₃ | N |
| 104 | CH≡CCH₂O | CH≡CCH₂O | CH₃O | CH₃O | CH |
| 105 | CH≡CCH₂O | CH≡CCH₂O | CH₃O | CH₃ | N |
| 106 | C₆H₅O | C₆H₅O | CH₃O | CH₃O | CH |
| 107 | C₆H₅O | C₆H₅O | CH₃O | CH₃ | N |
| 108 | CH₃CH=CHCH₂O | CH₃CH=CHCH₂O | CH₃O | CH₃O | CH |
| 109 | CH₃CH=CHCH₂O | CH₃CH=CHCH₂O | CH₃O | CH₃ | N |
| 110 | CH₂=CHCH₂O | n-C₃H₇O | CH₃O | CH₃O | CH |
| 111 | CH₂=CHCH₂O | n-C₃H₇O | CH₃O | CH₃ | N |
| 112 | CF₃CH₂O | C₆H₅O | CH₃O | CH₃O | CH |
| 113 | CF₃CH₂O | C₆H₅O | CH₃O | CH₃ | N |
| 114 | n-C₃H₇O | C₆H₅O | CH₃O | CH₃O | CH |
| 115 | n-C₃H₇O | C₆H₅O | CH₃O | CH₃ | N |
| 116 | CH₂=CHCH₂O | C₂H₅O | CH₃O | CH₃O | CH |
| 117 | CH₂=CHCH₂O | C₂H₅O | CH₃O | CH₃ | N |
| 118 | C₂H₅O | CHF₂O | CH₃O | CH₃O | CH |
| 119 | C₂H₅O | CHF₂O | CH₃O | CH₃ | N |
| 120 | CF₃CH₂O | CH₂=CHCH₂O | CH₃O | CH₃ | N |
| 121* | C₂H₅O | C₂H₅O | CH₃O | CH₃ | N |
| 122* | C₂H₅O | CF₃CH₂O | CH₃O | CH₃ | N |

*These two compounds have an N-methyl bridge (R₁ = CH₃)

The compounds of the invention may be prepared by a variety of methods and in a further aspect the invention provides methods for the preparation of compounds of formula I.

Conveniently the preparation of the compounds of the invention can be considered in three parts.

Part A involves the preparation of 5-pyrimidine-sulfonamides of the formula II

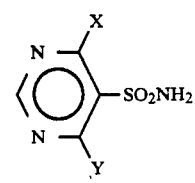

wherein X and Y are as defined above for formula I. The sulfonamides of formula II cannot generally be prepared by the traditional chlorosulfonation approach, but may usually be formed via the 5-mercaptopyrimidyl derivatives of formula III

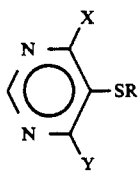

III wherein X and Y are as defined for formula I and R is hydrogen, cyano, benzyl or a suitable alkyl or substituted alkyl group. Thus, treatment of the mercaptopyrimidyl compounds III with chlorine in the presence of water leads to the corresponding 5-chlorosulfonylpyrimidines of formula IV

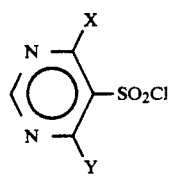

IV and treatment of the sulfonyl chlorides IV with either anhydrous or aqueous ammonia gives the compounds of formula II.

The chlorinolysis reaction is preferably carried out in the presence of a suitable organic solvent. Either a water miscible co-solvent such as acetic acid or the lower alcohols can be used, or a two-phase system with solvents such as the hydrocarbons, halocarbons or ethers may be employed. Preferably the reaction is carried out at or below ambient temperature ($-5°$ to $25°$ C.).

The conversion of the sulfonyl chlorides of formula IV into the sulfonamides II is conveniently carried out in a suitable organic solvent such as diethyl ether, acetonitrile, tetrahydrofuran or methylene chloride. The reaction is preferably carried out at reduced temperatures, for example, of from $-20°$ to $+10°$ C., and the amount of ammonia used may need to be controlled to avoid further reaction of the products.

The 5-mercaptopyrimidyl derivatives of formula III may be prepared by a number of methods including those described in the sections (i) to (iv) below.

(i) By condensing formamidine with suitable mercapto derivatives of alkyl malonates to give 4,6-dihydroxy-5-mercaptopyrimidines of formula V,

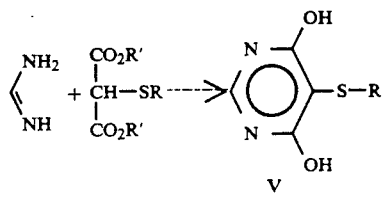

and then treatment of the dihydroxy compound of formula V with phosphorous oxychloride to give the 4,6-dichloro compounds of formula VI,

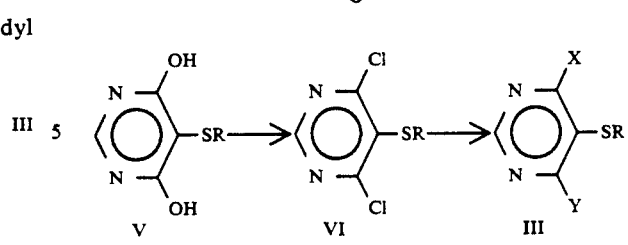

which may then be converted to the compounds of formula III by reaction with the appropriate nucleophiles $X^-$ and $Y^-$.

(ii) By the reaction of 5-halo-4,6-dihydroxypyrimidines of formula VII with suitable sulfur nucleophiles RSH to give the 4,6-dihydroxy-5-mercaptopyrimidines of formula V

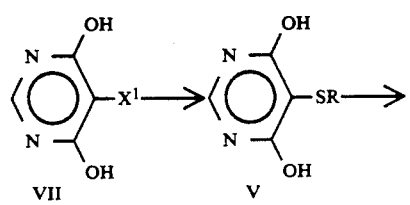

which can be converted to the compounds of formula III by the general method outlined in section (i) above.

(iii) By the reaction of 4,6-dihydroxypyrimidine with suitable sulfenyl chlorides RSCl to give the 4,6-dihydroxy-5-mercaptopyrimidines of formula V,

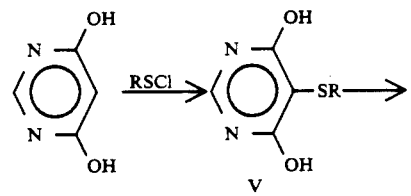

which can be converted to the compounds of formula III by the general approach given in section (i) above.

(iv) Treatment of the 4,6-dihydroxy-5-mercapto derivatives of formula V with certain difluorohalomethanes or various polyhaloethylene and propylene derivatives to give certain compounds of formula III

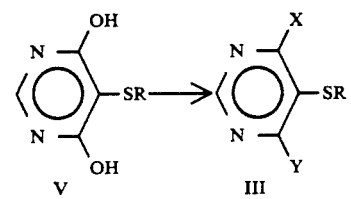

wherein for example X and Y are difluoromethoxy, 1,1,2,2-tetrafluoroethoxy or 2-chloro-1,1,2-trifluoroethoxy.

In section (i) above R is alkyl or benzyl and in sections (ii) and (iii) above, the definition of the group R in formula V is the same as defined for formula III above.

In section (i) the group R' represents $C_1$ to $C_4$ alkyl and in section (ii) the group X' denotes a halogen atom preferably chlorine or bromine.

An alternative method for the preparation of the sulfonamides of formula II is to treat a sulfonamide of formula VIII with the nucleophile $X^-$ and optionally a second nucleophile $Y^-$.

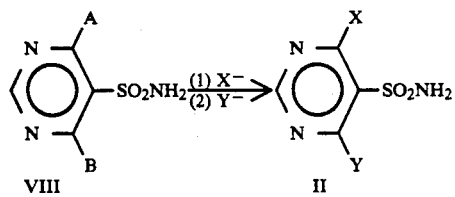

VIII    II

The groups A and B are leaving groups which can be selected for example from alkoxy groups such as those defined for X and Y in formula I, or A and B can be aryloxy and halogen substituents. The groups A and B are preferably chosen from phenoxy, chlorine, methoxy and haloalkoxy moieties.

The reactants are preferably used in substantially equimolar proportions and the reaction may be carried out in an inert solvent or by using an excess of the alcohol XH or YH as solvent. Examples of inert solvents include chlorinated hydrocarbons, ethers and alkyl nitriles.

Part B of the preparation of the compounds of the invention involves the preparation of various 2-aminopyrimidines and -s-triazines.

The heterocyclic amines of Formula IX can be prepared by methods known in the literature, or simple modifications thereof, by one skilled in the art.

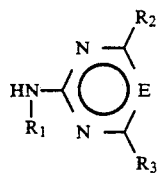

IX

For a review of the synthesis and reactions of 2-amino- and 2-methylaminopyrimidines (IX, E=CH) see *The Chemistry of Heterocyclic Compounds*, Vol. 16, Wiley Interscience, New York (1962). For a review of the synthesis and reactions of 2-amino- and 2-methylamino-s-triazines (IX, E=N) see *The Chemistry of Heterocyclic Compounds*, Vol. 13, Wiley-Interscience, New York (1959), and F C Schaefer and K R Huffman, *J. Org. Chem.*, 28, 1812 (1963).

Part C of the preparation of the compounds of the invention (formula I) involves the coupling of the sulfonamides of formula II with the heterocyclic amines of formula IX. The compounds of formula I can be prepared by one or more of the methods described below.

a) Many of the compounds of formula I can be prepared by reacting a sulfonylisocyanate or a sulfonylisothiocyanate of formula X with a heterocyclic amine of formula IX.

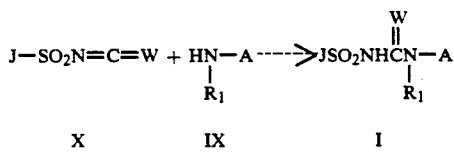

X    IX    I where J represents the system

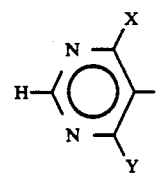

and A represents the system

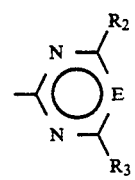

The reaction is carried out at 25° to 100° C. in an inert, aprotic solvent such as methylene chloride or xylene for 0.5 to 24 hours as taught in U.S. Pat. No. 4,127,405.

The intermediate sulfonylisocyanates (X, W=O) and isothiocyanates (X, W=S) are prepared by a variety of methods which are well known in the art and are described for example in European Patent Application 0 212 779 and the references cited therein.

b) Many of the compounds of formula I, where W is oxygen, can be prepared by reacting a phenyl carbamate of formula XI with a suitable amine of formula IX.

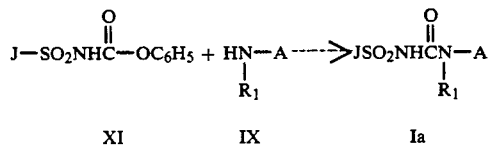

XI    IX    Ia

The reaction is carried out at 50° to 100° C. in a solvent such as dioxane for 0.5 to 24 hours. The required carbamates XI are prepared by reacting the corresponding sulfonamides II with diphenylcarbonate in the presence of a strong base.

c) Compounds of formula Ia can also be made by reacting a heterocyclic carbamate of formula XII with a suitable sulfonamide of formula II.

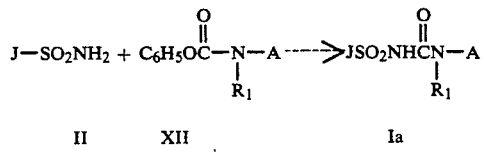

II    XII    Ia

The reaction is carried out at 0° to 100° C. in a solvent such as acetonitrile or dioxane in the presence of a non-nucleophilic base such as DBU for 0.2 to 24 hours. The required phenylcarbamates XII are prepared by reacting the corresponding heterocyclic amines IX with diphenylcarbonate or phenylchloroformate in the presence of a strong base.

d) Some of the compounds of the invention of formula Ib can be prepared by reacting a sulfonamide II with a heterocyclic isocyanate or isothiocyanate of formula XIII.

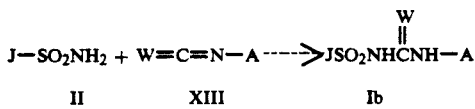

| II | XIII | Ib |

The reaction is carried out at 25° to 80° C. in an inert, aprotic solvent such as acetone or acetonitrile in the presence of a base such as potassium carbonate for 0.5 to 24 hours. The required heterocyclic isocyanates and iso-thiocyanates XIII are prepared from the corresponding amines $H_2NA$ which would be known to one skilled in the art as taught in European Patent Application 0 035 893.

In each of parts b), c) and d) above the groups J, W, A and $R_1$ are as previously described.

Certain of the intermediate compounds of formulae II, III, IV, V and VI are novel compounds and therefore in further embodiments the invention provides novel compounds of formulae II, III, IV, V and VI and processes for the preparation thereof.

Agriculturally suitable salts of compounds of Formula I are also useful herbicides and can be prepared in a number of ways known to the art. For example, metal salts can be made by contacting compounds of formula I with a solution of an alkali or alkaline earth metal salt having a sufficiently basic anion (e.g. hydroxide, alkoxide or carbonate). Quaternary amine salts can be made by similar techniques.

Salts of compounds of Formula I can also be prepared by exchange of one cation to another. Cationic exchange can be effected by direct treatment of an aqueous solution of a salt of a compound of Formula I, (e.g, alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula I, (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I, with a suitable acid, e.g., p-toluenesulfonic acid, trichloroacetic acid or the like.

The compounds of Formula I are active as herbicides and therefore, in a further aspect the invention provides a process for severely damaging or killing unwanted plants which process comprises applying to the plant, or to the growth medium of the plants, an effective amount of a compound of Formula I as hereinabove defined.

The compounds of Formula I may be applied directly to the plant (post-emergence application) or to the soil before the emergence of the plant (pre-emergence application). The compounds of Formula I are active against a broad range of weed species including monocotyledonous and dicotyledonous species. Some of the compound show selectivity towards certain crop species. A number show selectivity towards cereals, a particularly commercially valuable trait.

Moreover, certain of the compounds of formula I are selectively active within the group of monocotyledonous plants and may be used at a rate sufficient to control monocotyledonous weeds in cultivated crops, especially wild grasses in cereal crops. Certain of such compounds of the invention are especially useful in the control of wild grasses such as wild oats and rye grass in crops of cultivated monocotyledonous plants such as wheat.

Accordingly, in yet a further aspect the invention provides a process for suppressing monocotyledonous and dicotyledonous weeds in cultivated crops, especially cereal crops, which process comprises applying to the crop, or to the growth medium of the crop, a compound of formula I, as hereinbefore defined, in an amount sufficient to severely damage or kill the weeds but insufficient to damage the crop substantially.

The compounds of Formula I may be used on their own to inhibit the growth of, severely damage, or kill plants but are preferably used in the form of a composition comprising a compound of the invention in admixture with a carrier comprising a solid or liquid diluent. Therefore, in yet a further aspect the invention provides growth inhibiting, plant damaging, or plant killing compositions comprising a compound of Formula I as hereinbefore defined and an inert carrier therefor.

Certain of the compounds of Formula I exhibit useful plant growth regulating activity.

Plant growth regulating effects may be manifested in a number of ways. For example, suppression of apical dominance, stimulation of auxiliary bud growth, stimulation of early flowering and seed formation, enhancement of flowering and increase in seed yield, stem thickenings, stem shortening and tillering.

Accordingly in a still further aspect the invention provides a process for regulating the growth of a plant which process comprises applying to the plant, to the seed of the plant, or to the growth medium of the plant, an effective amount of a compound of Formula I, as hereinbefore defined.

To effect the plant growth regulating process of the present invention the compounds of Formula I may be applied directly to the plant (post-emergence application) or to the seed or soil before the emergence of the plant (pre-emergence) application.

The compounds of Formula I may be used on their own to regulate the growth of plants but in general are preferably used in the form of a composition comprising a compound of the invention in admixture with a carrier comprising a solid or liquid diluent. Therefore, in a still further aspect the invention provides plant growth regulating compositions comprising a compound of Formula I as hereinbefore defined and an inert carrier therefor.

The compositions of the present invention may be in the form of solids, liquids or pastes. The compositions include both dilute compositions which are ready for immediate use and concentrated compositions which may require dilution before use. Therefore, the concentration of the active ingredient in the compositions of the present invention will vary depending on the types of formulation and whether the composition is ready for use such as, for example, a dust formulation or an aqueous emulsion or whether the composition is a concentrate such as, for example, an emulsifiable concentrate or a wettable powder, which is suitable for dilution before use. In general, the composition of the present invention comprise from 1 ppm to 99% by weight of active ingredient.

The solid compositions may be in the form of powders, dusts, pellets, grains, and granules wherein the active ingredient is mixed with a solid diluent. Powders and dusts may be prepared by mixing or grinding the active ingredient with a solid carrier to give a finely divided composition. Granules, grains and pellets may be prepared by bonding the active ingredient to a solid carrier, for example, by coating or impregnating the preformed granular solid carrier with the active ingredient or by agglomeration techniques.

Examples of solid carriers include: mineral earths and clays such as, for example, kaolin, bentonite, kieselguhr, Fuller's earth, Attaclay, diatomaceous earth, bole, loess, talc, chalk, dolomite, limestone, lime, calcium carbonate, gypsum, calcium sulfate, pyrophyllite, silicic acid, silicates and silica gels, fertilizers such as, for example, ammonium sulfate, ammonium phosphate, ammonium nitrate and urea; natural products of vegetable origin such as, for example, grain meals and flours, bark meals, wood meals, nutshell meals and cellulosic powders; and synthetic polymeric materials such as, for example, ground or powdered plastics and resins.

Alternatively, the solid compositions may be in the form of dispersible or wettable dusts, powders, granules or grains wherein the active ingredient and the solid carrier are combined with one or more surface active agents which act as wetting, emulsifying and/or dispersing agents to facilitate the dispersion of the active ingredient in liquid.

Examples of surface active agents include those of the cationic, anionic and non-ionic type. Cationic surface active agents include quaternary ammonium compounds, for example, the long chain alkylammonium salts such as cetyltrimethylammonium bromide. Anionic surface active agents include: soaps or the alkali metal, alkaline earth metal and ammonium salts of fatty acids; the alkali metal, alkaline earth metal and ammonium salts of ligninsulfonic acid; the alkali metal, alkaline earth metal and ammonium salts of arylsulfonic acids including the salts of naphthalenesulfonic acids such as butylnaphthalenesulfonic acids, the di- and tri-isopropylnaphthalenesulfonic acids, the salts of the condensation products of sulfonated naphthalene and naphthalene derivatives with formaldehyde, the salts of the condensation products of sulfonated naphthalene and naphthalene derivatives with phenol and formaldehyde, and the salts of alkylarylbenzenesulfonic acids such as dodecylbenzenesulfonic acid; the alkali metal, alkaline earth metal and ammonium salts of the long chain mono esters of sulfuric acid or alkylsulfates such as laurylsulfate and the mono esters of sulfuric acid with fatty alcohol glycol ethers. Nonionic surface active agents include: the condensation products of ethylene oxide with phenols and alkylphenols such as isooctylphenol, octylphenol and nonylphenol; the condensation products of ethylene oxide with castor oil; the partial esters derived from long chain fatty acids and hexitol anhydrides, for example sorbitan monolaurate, and their condensation products with ethylene oxide; ethylene oxide/propylene oxide block copolymers; lauryl alcohol polyglycol ether acetal; and the lecithins.

The liquid compositions may comprise a solution or dispersions of the active ingredient in a liquid carrier optionally containing one or more surface active agents which act as wetting, emulsifying and/or dispersing agents. Examples of liquid carriers include: water, mineral oil fractions such as, for example, kerosene, solvent naphtha, petroleum, coal tar oils and aromatic petroleum fractions; aliphatic, cycloaliphatic and aromatic hydrocarbons such as, for example, paraffin, cyclohexane, toluene, the xylenes, tetrahydronaphthalene and alkylated naphthalenes; alcohols such as, for example, methanol, ethanol, propanol, isopropanol, butanol, cyclohexanol and propylene glycol; ketones such as, for example, dimethylformamide, dimethysulfoxide, N-methylpyrrolidone and sulfolane.

A preferred liquid composition comprises an aqueous suspension, dispersion or emulsion of the active ingredient which is suitable for application by spraying, atomizing or watering. Such aqueous compositions are generally prepared by mixing concentrated compositions with water. Suitable concentrated compositions include emulsion concentrates, pastes, oil dispersions, aqueous suspensions and wettable powders. The concentrates are usually required to withstand storage for prolonged periods and after such storage to be capable of dilution with water to form aqueous preparations which remain homogeneous for a sufficient time to enable them to be applied by conventional spray equipment. The concentrates conveniently contain from 10 to 99%, preferably 10 to 60% by weight of active ingredient.

Emulsion or emulsifiable concentrates are conveniently prepared by dissolving the active ingredient in an organic solvent containing one or more surface active agents and optionally an oil. Oil dispersions may be prepared by grinding together the active ingredient, a hydrocarbon oil, and one or more surface active agents. Aqueous suspension concentrates may conveniently be prepared by ball milling a mixture of the active agent and preferably at least one suspending agent. Suitable suspending agents include: hydrophilic colloids such as, for example, poly(N-vinylpyrrolidone), sodium carboxymethylcellulose and the vegetable gums, gum acacia and gum tragacanth; hydrated colloidal mineral silicates such as, for example, montmorillonite, beidellite, nontronite, hectorite, saponite, sauconite and bentonite; other cellulose derivatives; and poly(vinyl alcohol).

Wettable powder concentrates may conveniently be prepared by blending together the active ingredient, one or more surface active agents, one or more solid carriers and optionally one or more suspending agents and grinding the mixture to give a powder having the required particle size.

The aqueous suspensions, dispersions or emulsions may be prepared from the concentrated compositions by mixing the concentrated compositions with water optionally containing surface active agents and/or oils.

It should be noted that the compounds of the invention of formula I are acidic. Therefore, the compounds of formula I may be formulated and applied as the salts of organic or inorganic bases. In formulating and employing the compounds of formula I in the form of their salts either the salts per se may be used in the formulation or the compounds of formula I may be used in the formulation and the salts generated in situ by the use of the appropriate organic or inorganic base.

The mode of application of the compositions of the invention will depend to a large extent on the type of composition used and the facilities available for its application. Solid compositions may be applied by dusting or any other suitable means for broadcasting or spreading the solid. Liquid-compositions may be applied by spraying, atomizing, watering, introduction into the irrigation water, or any other suitable means for broadcasting or spreading the liquid.

The rate or application of the compounds of the invention will depend on a number of factors including, for example, the compound chosen for use, the identity of the plants whose growth is to be inhibited, the formulations selected for use and whether the compound is to be applied for foliage or root uptake. As a general guide, however, an application rate of from 0.001 to 10 kilograms per hectare is suitable while from 0.01 to 5.0 kilogram per hectare may be preferred.

The composition of the invention may comprise, in addition to one or more compounds of the invention, one or more compounds not of the invention but which possess biological activity. As a result, in certain applications the herbicidal use of the compounds of the invention alone may not be sufficient to protect a crop. Accordingly in yet a still further embodiment the invention provides a herbicidal composition comprising a mixture of at least one herbicidal compound of formula I as hereinbefore defined with at least one other herbicide.

The other herbicide may be any herbicide not having the formula I. It will generally be a herbicide having a complementary action. For example, one preferred class is of mixtures comprising a herbicide active against broad-leaved weeds. A second preferred class is of mixtures comprising a contact herbicide.

Example of useful complementary herbicides include:
A. benzo-2,1,3-thiadiazin-4-one-2,2-dioxides such as 3-isopropylbenzo-2,1,3-thiadiazin-4-one-2,2-dioxide (common name bentazon);
B. hormone herbicides and in particular the phenoxyalkanoic acids such as 4-chloro-2-methylphenoxy acetic acid (common name MCPA), 2-(2,4-dichlorophenoxy)propionic acid (common name dichlorprop), 2,4-dichlorophenoxy acetic acid (common name 2,4,D), 2,4,5-trichlorophenoxyacetic acid (common name 2,4,5-T), 4-(4-chloro-2-methylphenoxy) butyric acid (common name MCPB), 4-(2,4-dichloro-phenoxy)butyric acid (common name 2,4-DB), 2-(4-chloro-2-methylphenoxy) propionic acid (common name mecoprop), and their derivatives (e.g. salts, esters, amides and the like);
C. 3-[4-(4-halophenoxy)phenyl]-1,1-dialkylureas such as 3-[4-(4-chlorophenoxy)phenyl]-1,1-dimethylurea (common name chloroxuron);
D. dinitrophenols and their derivatives (e.g. acetates) such as 2-methyl-4,6-dintrophenol (common name DNOC), 2-tertiarybutyl-4,6-dintrophenol (common name dinoterb), 2-secondarybutyl-4,6-dinitrophenol (common name dinoseb) and its ester dinoseb acetate;
E. dinitroaniline herbicides such as N', N'-diethyl-2,6-dinitro-4-trifluoromethyl-m-phenylenediamine (common name dinitramine), 2,6-dinitro-N,N-dipropyl-4-trifluoromethylaniline (common name trifluralin) and 4-methylsulfonyl-2,6-dinitro-N,N-dipropylaniline (common name nitralin);
F. phenylurea herbicides such as N'-(3,4-dichlorophenyl)-N,N-dimethylurea (common name diuron) and N,N-dimethyl-N'-[3-trifluoromethyl)phenyl]urea (common name fluometuron);
G. phenylcarbamoyloxyphenylcarbamates such as 3-[(methoxycarbonyl)amino]phenyl (3-methylphenyl)-carbamate (common name phenmedipham) and 3-[(ethoxycarbonylamino]phenyl phenylcarbamade (common name desmedipham);
H. 2-phenylpyridazin-3-ones such as 5-amino-4-chloro-2-phenylpyridazin-3-one (common name pyrazon);
I. uracil herbicides such as 3-cyclohexyl-5,6-trimethyleneuracil (common name lenacil), 5-bromo-3-sec-butyl-6-methyluracil (common name bromacil) and 3-tert-butyl-5-chloro-6-methyluracil (common name terbacil);
J. triazine herbicides such as 2-chloro-4-ethylamino-6-(iso-propylamino)-1,3,5-triazine (common name atrazine). 2-chloro-4,6-di(ethylamino)-1,3,5-triazine (common name simazine) and 2-azido-4-(isopropylamino)-6-methylthio-1,3,5-triazine (common name aziproptryne);
K. 1-alkoxy-2-alkyl-3-phenylurea herbicides such as 3-(3,4-dichlorophenyl)-1-methoxy-1-methylurea (common name linuron), 3-(4-chlorophenyl)-1-methoxy-1-methylurea (common name monolinuron) and 3-(4-bromo-4-chlorophenyl)-1-methoxy-1-methylurea (common name chlorobromuron);
L. Pyridine herbicides such as 3,6-dichloropicolinic acid (common name clopyralid) and 4-amino-3,5,6-trichloropicolinic acid (common name picloram);
M. 1,2,4-triazin-5-one herbicides such as 4-amino-4,5-dihydro-3-methyl-6-phenyl-1,2,4-triazine-5-one (common name metamitron) and 4-amino-6-tert-butyl 4,5-dihydro-3-methylthio-1,3,4-triazin-5-one (common name metribuzin);
N. benzoic acid herbicides such as 2,3,6-trichlorobenzoic acid (common name 2,3,6-TBA), 3,6-dichloro-2-methoxybenzoic acid (common name dicamba) and 3-amino-2,5-dichlorobenzoic acid (common name chloramben);
O. anilide herbicides such as N-butoxymethyl-α-chloro-2',6'-diethylacetanilide (common name butachlor), the corresponding N-methoxy compound (common name alachlor), the corresponding N-isopropyl compound common name propachlor) and 3',4'-dichloropropionanilide (common name propanil);
P. dihalobenzonitrile herbicides such as 2,6-dichlorobenzonitrile (common name dichlobenil), 3,5-dibromo-4-hydroxy benzonitrile (common name bromoxynil) and 3,5-diiodo-4-hydroxybenzonitrile (common name ioxynil);
Q. haloalkanoic herbicides such as 2,2-dichloropropionic acid (common name dalapon), trichloroacetic acid (common name TCA) and salts thereof;
R. diphenylether herbicides such as 4-nitrophenyl 2-nitro-4-trifluoromethylphenyl ether (common name fluorodifen), methyl 5-(2,4-dichlorophenoxy)-2-nitrobenzoate (common name bifenox), 2-nitro-5-(2-chloro-4-trifluoromethylphenoxy)benzoic acid and 2-chloro-4-trifluoromethylphenyl 3-ethoxy-4-nitrophenyl ether;
S. N-(heteroarylaminocarbonyl)benzenesulfonamides such as 2-chloro-N-[(4-methoxy-6-methyl-1,3,5-triazin-2-yl)amino carbonyl]benzenesulfonamie (commonly known as DPX 4189);

T. Aryloxyphenoxypropionate herbicides such as butyl 2-[4-(5-trifluoromethyl-2-pyridyloxy) phenoxy]propionate (common name fluazifop) and methyl 2-[4-(2,4-dichlorophenoxy) phenoxy]propionate (common name diclofop); and
U. miscellaneous herbicides including N,N-dimethyldiphenylacetamide (common name diphenamid), N-(1-naphthyl)phthalamic acid (common name naptalam) and 3-amino-1,2,4-triazole.

Example of useful contact herbicides include:
V. bipyridylium herbicides such as those in which the active entity is the 1,1'-dimethyl-4,4'-dipyridylium ion (common name paraquat) and those in which the active entity is the 1,1'-ethylene-2,2'-dipyridylium ion (common name diquat);
W. organoarsenical herbicides such as monosodium methanearsonate (common name MSMA); and
X. amino acid herbicides such as N-(phosphonomethyl)-glycine (common name glyphosate) and its salts and esters.

The compounds of this invention and their preparation are further illustrated by the following examples.

EXAMPLE 1

N-[(4-Methoxy-6-methyl-1,3,5-triazin-2-yl)aminocarbonyl]-4,6-diethoxypyrimidine-5-sulfonamide (4)

(i) 4,6-Dihydroxy-5-benzylthiopyrimidine

Benzylmercaptan (6 ml, 0.05 mole) was added to a stirred and heated (90°) suspension of 5-bromo-4,6-dihydroxypyrimidine (9.5 g, 0.05 mole) and potassium carbonate (7.5 g, 0.055 mole) in dimethylformamide (25 ml). The reaction mixture was stirred and heated at 95–105° C. under an atmosphere of dry nitrogen for 3.5 hours. The mixture was poured into ice cold water (400 ml) with vigorous stirring and then acidified to pH 1 with hydrochloric acid. After stirring for 0.5 hours the suspension was filtered and the solid which was collected was rinsed several times with n-hexane and diethyl ether. The remaining brown solid was air dried to give 4,6-dihydroxy-5-benzylthiopyrimidine (5.5 g 50%) PMR spectrum: ($d_6$ DMSO) 3.96 (S, 2h); 7.2 (bm, 5H); 8.11 (s, 1H); 12.2 (bs, 2H).

(ii) 4,6-Dichloro-5-benzylthiopyrimidine

A mixture of phosphorous oxychloride (40 ml) and 4,6-dihydroxy-5-benzylthiopyrimidine (5 g) was stirred and heated under reflux for 3 hours. Excess phosphorous oxychloride was removed by distillation under reduced pressure and the residue was cooled, dissolved in chloroform (200 ml) and the chloroform solution was washed with water (3×200 ml). The chloroform layer was separated, dried ($MgSO_4$) and then concentrated to give a brown oil (4.1 g) which was purified by column chromatography (silica gel, hexane-chloroform (1:1) to give the dichloropyrimidine as nearly colourless low melting point solid (3.3 g). PMR spectrum: ($CDCl_3$) 4.18 (s, 2H); 7.2 (bm, 5H); 8.60 (s, 1H).

(iii) 4,6-Diethoxy-5-benzylthiopyrimidine

Sodium metal (0.50 g, 22 mmole) was dissolved in ethanol (100 ml) and the solution was added to 4,6-dichloro-5-benzylthiopyrimidine (2.7 g, 10 mmole). The mixture was stirred and heated under reflux for one hour by which time thin layer chromatography showed the formation of the product. After standing at room temperature for 15 hours the solution was concentrated on a rotary evaporator and then the residue partitioned between water and methylene chloride. The methylene chloride layer was separated, dried ($MgSO_4$) and evaporated to give the title diethoxypyrimidine as an almost colourless low-melting point solid (2.6 g). PMR spectrum: ($CDCL_3$) 1.36 (t, 6H); 3.99 (s, 2H); 4.40 (q, 4H); 7.2 (bm, 5H); 8.26 (s, 1H).

(iv) 4,6-Diethoxypyrimidine-5-sulfonamide

A suspension of 4,6-diethoxy-5-benzylthiopyrimidine (2 g) in acetic acid (50 ml) and water (50 ml) was vigorously stirred and cooled to 5° C. Chlorine gas was bubbled into the stirred suspension for approximately 0.5 hour. After a few minutes further stirring below 5° C. the reaction mixture was poured into ice-water (200 ml) and extracted with ether (2×100 mi). The ether extracts were separated, dried ($MgSO_4$) and evaporated to give the crude pyrimidine-5-sulfonylchloride as a pale yellow oil. The sulfonylchloride was not fully characterized, but was immediately dissolved in acetonitrile (50 ml) and the solution cooled in ice and treated with ammonia gas for several minutes. The acetonitrile and excess ammonia were removed on a rotary evaporator and the residue was partitioned between water and ethyl acetate. The ethyl acetate layer was dried and concentrated until a white solid began to crystallize. Trituration with ether and filtration allowed isolation of the title sulfonamide as a white solid (500 mg). Pmr spectrum: ($CDCl_3$) 1.44 (t, 6H); 4.56 (q, 4H); 6.0 (brs, 2H); 8.39 (s, 1H).

(v) N-[(4-Methoxy-6-methyl-1,3,5-triazin-2-yl) aminocarbonyl]-4,6-diethoxypyrimidine-5-sulfonamide (4)

N-(2-Amino-4-methoxy-6-methyl-1,3,5-triazinyl) phenylcarbamate (260 mg, 1.0 mmol) and 4,6-diethoxypyrimidine-5-sulfonamide (250 mg, 1.0 mmole) were dissolved in dimethyl formamide (5 ml). The solution was cooled in ice and 1,8-diazobicyclo[5.4.0]undec-7-ane (DBU) (150 mg, 1 mmole) was added with stirring. After 0.5 hour at ice temperature and a further hour without cooling the reaction mixture was poured into ice-water (100 ml) and the aqueous solution was acidified to pH 4 with stirring. The white precipitate was collected by filtration and air dried to give compound No. 4 as a colourless powder (390 mg) which was identified by its proton magnetic resonance spectrum: ($d_6$ DMSO) 1.24 (t, 6H); 2.47 (s, 3H); 3.98 (s, 3H); 4.47 (q, 4H); 8.62 (s, 1H); 11.09 (brs, 1H); 12.47 (brs, 1H).

EXAMPLE 2

N-[(4.6-Dimethoxypyrimidin-2-yl)amino carbonyl]-4,6-bis (difluoromethoxy)pyrimidine-5-sulfonamide (27)

(i) 4,6-Bis(difluoromethoxy)-5-benzylthio pyrimidine

A solution of sodium hydroxide (100 g) in water (250 ml) was added with stirring to a suspension of 4,6-dihydroxy-5-benzylthiopyrimidine (23 g) in dioxane (500 ml). The mixture was stirred vigorously and heated to 70° C. at which temperature chlorodifluoromethane was bubbled into the solution for a period of 1.5 hours. The reaction mixture was then allowed to cool to room temperature and extracted in a separating funnel with n-hexane (2×300 ml). The combined organic extracts were dried ($MgSO_4$) filtered and evaporated on a rotary evaporator to give 4,6-bis(difluoromethoxy)-5-benzylthiopyrimidine (1.8 g). PMR spectrum: (CDCl$_3$) 4.10 (s, 2H); 7.2 (bm, 5H); 7.38 (t, 2H); 8.28 (s, 1H).

(ii) 4,6-Bis(difluoromethoxy)pyrimidine-5-sulfonamide

The benzylthioether from part (i) was converted into the corresponding sulfonamide following essentially the same conditions described in Example 1, part (iv). The sulfonamide was isolated as a colourless crystalline solid, PMR spectrum: (d$_6$ acetone) 7.18 (bs); 7.80 (t, 2H); 8.73 (s, 1H).

(iii) 4,6-Bis(difluoromethoxy)pyrimidine-5-sulfonamide (250 mg) and N-(4,6-dimethoxypyrimidin-2-yl)phenyl carbamate (280 mg) were reacted together following the conditions described in Example 1, part (v). The product, sulfonylurea (27), was characterized by its PMR spectrum which is included in Example 4, Table 2 below.

EXAMPLE 3

N-[(4,6-Dimethoxypyrimidin-2-yl)aminocarbonyl]-4,6-diallyloxypyrimidine-5-sulfonamide (102)

(i) 4,6-diallyloxypyrimidine-5-sulfonamide

A solution of sodium metal (200 mg) and 4,6-dimethoxypyrimidine-5-sulfonamide (800 mg) in allyl alcohol (5 ml) was boiled under reflux conditions for 8 hours. Thin-layer chromatography showed the formation of a new higher RF product. Excess allyl alcohol was removed on a rotary evaporator and the residue was partitioned between water (pH 3) and chloroform (100 ml). The chloroform layer was dried (MgSO$_4$) and evaporated to give crude 4,6-diallyloxypyrimidine-5-sulfonamide which was purified by passage through a short column of silica gel. The pure sulfonamide was obtained as a colourless crystalline solid (0.70 g), PMR spectrum: (CDCl$_3$) 5.0 (d, 4H); 5.32 (d, 2H); 5.4–5.5 (m, 4H); 5.97–6.12 (m, 2H); 8.41 (s, 1H).

(ii) 4,6-Diallyloxypyrimidine-5-sulfonamide and N-(4,6-dimethoxypyrimidin-2-yl)phenyl carbamate were reacted together following the conditions described in Example 1, part (v). The product sulfonylurea, compound No. 102 of the invention was characterized by its PMR spectrum which is included in Example 4, Table 2 below.

EXAMPLE 4

(i) Compounds Nos. 2, 3, 5, 9–12, 14, 16–19, 23, 25, 38, 42, 44, 52, 62, 64, 75–81, 83–85, 87–91, 93–99, 101, 106–107, 112–113, 115, 120–122 were each prepared starting from 4,6-dichloro-5-benzylthiopyrimidine and proceeding via the appropriate 4,6-disubstituted-5-sulfonamido pyrimidine following a similar method to that described in Example 1, parts (iii) to (v).

(ii) Compounds No's 118 and 119 were prepared starting from 4-ethoxy-6-hydroxy-5-benzylthiopyrimidine and proceeding in a manner analogous to that given in Example 2, parts (i) to (iii).

(iii) Compounds No's 103, 104, 105, 108, 109, 111 and 117 were each prepared starting from a 4,6-disubstituted pyrimidine-5-sulfonamide and displacing one or both of the 4,6 substituents with the anion of the appropriate alcohol following similar conditions to those given in Example 3, parts (i) and (ii).

Each compound was characterized in part by its proton magnetic resonance spectrum and details are recorded in Table 2 below.

TABLE 2

| Compound No. | Proton Chemical Shift δ in ppm (d$_6$ DMSO unless noted) |
|---|---|
| 2 | (CDCl$_3$)1.33(t, 6H); 3.90(s, 6H); 4.52(q, 4H); 5.8(s, 1H); 7.4(s, 1H); 8.4(s, 1H); 12.7(s, 1H). |
| 3 | 1.20(t, 6H); 2.37(s, 3H); 3.92(s, 3H); 4.45(q, 4H); 6.58(s, 1H); 8.61 (s, 1H); 10.62(br s, 1H); 13.17(br s, 1H). |
| 5 | (d$_6$ acetone)1.31(t, 6H); 4.05 (s, 3H); 4.53(q, 4H); 6.71(s, 1H); 8.50(s, 1H); 9.58(br s, 1H); 12.12 (bs, 1H). |
| 9 | 3.9(s, 6H); 5.2(q, 4H); 6.0(s, 1H); 8.8(s, 1H); 10.7(br s, 1H); 13.0(br s, 1H). |
| 10 | (CDCl$_3$)2.42(s, 3H); 3,94(s, 3H); 4.93(q, 4H); 6.30(s, 1H); 8.50(s, 1H); 13.41(br s, 1H). |
| 11 | 2.46(s, 3H); 3.98(s, 3H); 5.25(q, 4H); 8.82(s, 1H); 11.17(br s, 1H); 12.80(br s, 1H). |
| 12 | 3.98(s, 3H); 5.21(q, 4H); 6.89(s, 1H); 8.80(s, 1H); 10.92(br s, 1H); 12.30(br s 1H). |
| 14 | (CDCl$_3$)4.94(q, 4H); 5.90(s, 1H); 7.35(t, 2H); 8.62(s, 1H); 12.7(s, 1H). |
| 16 | 4.02(s, 6H); 4.59(q, 2H); 5.29(q, 2H); 6.14(s, 1H); 8.82(s, 1H); 10.80 (s, 1H); 12.99(s, 1H); |
| 17 | (CDCl$_3$)2.42(s, 3H); 3.94(s, 3H); 4.57(q, 2H); 4.87(q, 2H); 6.29 (s, 1H); 8.44(s, 1H); 13.17(brs, 1H); |
| 18 | 1.24(t, 3H); 2.46(s, 3H); 3.98(s, 3H); 4.50(q, 2H); 5.13(q, 2H); 8.72 (s, 1H); 11.13(br s, 1H); 12.62(br s, 1H); |
| 19 | 1.24(t, 3H); 3.98(s, 3H); 4.51(q, 2H); 5.18(q, 2H); 6.89(s, 1H); 8.70(s, 1H); 10.86(s, 1H); 12.16(s, 1H); |
| 23 | (CDCl$_3$)3.27(s, 6H); 3.67(t, 4H); 3.97(s, 6H); 4.63(t, 4H); 5.80(s, 1H); 8.42(s, 1H); 12.76(s, 1H). |
| 25 | 2.58(s, 3H); 3.28(s, 6H); 3.69(t, 4H); 4.06(s, 3H); 4.64(t, 4H); 7.62 (br s, 1H); 8.43(s, 1H); 12.38(br s 1H). |
| 27 | (d$_6$ acetone); 3.97(s, 6H); 5.90(s, 1H); 7.83(t, 2H); 8.82(s, 1H); 9.58 (s, 1H); 13.33(s, 1H); |
| 38 | 3.91(s, 6H); 3.96(s, 3H); 4.44(q, 2H); 6.03(s, 1H); 8.64(s, 1H); 10.65(s, 1H); 12.80(s, 1H); |
| 40 | 1.21(t, 3H); 2.47(s, 3H); 3.98(s, 6H); 4.46(q, 2H); 8.65(s, 1H); 11.0 (br s, 1H); 12.50(br s, 1H); |
| 42 | (CDCl$_3$)3.96(s, 6H); 4.12(s, 3H); 4.89(q, 2H); 5.80(s, 1H); 7.36(s, 1H); 8.48(s, 1H); 12.86(s, 1H); |
| 44 | 2.46(s, 3H); 3.97(s, 3H); 4.02(s, 3H); 5.19(q, 2H); 8.74(s, 1H); 11.07(br s, 1H); 12.66(br s, 1H); |
| 52 | 2.47(s, 3H); 3.11(s, 3H); 3.55(s, 2H); 3.98(s, 6H); 4.55(s, 2H); 8.65(s, 1H); 11.0(br s, 1H); 12.55(s, 1H); |
| 62 | (d$_6$ acetone)1.26(d, 6H); 3.98(s, 6H); 4.02(s, 3H); 5.54(m, 1H); 5.90 (s, 1H); 8.51(s, 1H); 9.32(s, 1H); 12.70(s, 1H); |
| 64 | 1.21(d, 6H); 2.48(s, 3H); 3.99(s, H); 5.45(m, 1H); 8.64(s, 1H); 11.11 s, 1H); 12.43(s, 1H). |
| 75 | 1.25(t, 3H); 2.47(s, 3H); 3.15(s, 3H); 3.57(t, 2H); 3.95(s, 3H); 4.47 (q, 2H); 4.55(t, 2H); 8.63(s, 1H); 11.08(brs, 1H); 12.52(brs, 1H). |
| 76 | 3.11(s, 3H); 3.53(s, 2H); 3.92(s, 6H); 4.57(t, 2H); 5.18(q, 2H); 6.03 |

TABLE 2-continued

| Compound No. | Proton Chemical Shift δ in ppm (d₆ DMSO unless noted) |
|---|---|
|  | (s, 1H); 8.72(s, 1H); 10.68(brs, 1H); 12.93(brs, 1H). |
| 77 | 2.47(s, 3H); 3.12(s, 3H); 3.57(t, 2H); 3.98(s, 3H); 4.59(t, 2H); 5.15 (q, 2H); 8.72(s, 1H); 11.12(brs, 1H); 12.67(Brs, 1H). |
| 78 | 1.20(d, 12H); 3.92(s, 6H); 5.45(q, 2H); 6.06(s, 1H); 8.59(s, 1H); 10.70(brs, 1H); 12.69(brs, 1H). |
| 79 | 1.23(d, 12H); 2.48(s, 3H); 3.99(s, 3H); 5.44(q, 2H); 8.60(s, 1H); 11.13(brs, 1H); 12.36(s, 1H). |
| 80 | (CDCl₃)0.96(t, 6H); 1.75(sextet, 4H); 3.95(s, 6H); 4.4(t, 4H); 5.80 (s, 1H); 8.4(s, 1H); 12.0(s, 1H); 12.6(s, 1H). |
| 81 | (d₆ acetone)1.00(t, 6H); 1.76 (m, 4H); 2.53(s, 3H); 4.03(s, 3H); 4.44(t, 4H); 8.50(s, 1H); 9.72(s, 1H); 12.48(s, 1H); |
| 83 | 1.23(d, 6H); 1.25(t, 3H); 2.50(s, 3H); 3.99(s, 3H); 4.48(q, 2H); 5.44(m, 1H); 8.61(s, 1H); 11.11(s, 1H); 12.40(s, 1H); |
| 84 | (d₆ acetone)0.96(t, 3H); 1.27(t, 3H); 1.74(m, 2H); 3.97(s, 6H); 4.44(t, 2H); 4.52(q, 2H); 5.89(s, 1H); 8.49(s, 1H); 9.27(s, 1H); 12.70(s, 1H); |
| 85 | (d₆ acetone)0.99(t, 3H); 1.31(t, 3H); 1.76(m, 2H); 2.52(s, 3H); 4.04 (s, 3H); 4.44(t, 2H); 4.54(q, 2H); 8.49(s, 1H); 9.70(s, 1H); 12.45 (s, 1H); |
| 87 | 1.26(t, 3H); 2.46(s, 3H); 3.98(s, 3H); 4.55(q, 2H); 7.39(m, 1H); 8.80(s, 1H); 11.12(s, 1H); 12.69 (s, 1H); |
| 88 | (d₆ acetone)0.88(t, 3H); 1.28(t, 3H); 1.42(m, 2H); 1.68(m, 2H); 3.98(s, 6H); 4.50(q, 2H); 4.54 (t, 2H); 5.89(s, 1H); 8.49(s, 1H); 9.28(s, 1H); 12.69(s, 1H); |
| 89 | (d₆ acetone)0.89(t, 3H); 1.31 (t, 3H); 1.45(m, 2H); 1.69(m, 2H); 2.52(s, 3H); 4.04(s, 3H); 4.50(q, 2H); 4.54(t, 2H); 8.49(s, 1H); 9.64 (s, 1H); 12.45(s, 1H); |
| 90 | (d₆ acetone)1.33(t, 3H); 3.93(s, 6H); 4.58(q, 2H); 5.78(s, 1H); 7.12(m, 2H); 7.25(m, 1H); 7.40(m, 2H); 8.40(s, 1H); 9.39(s, 1H); 12.8 (br s, 1H); |
| 91 | (d₆ acetone)1.36(t, 3H); 2.42(s, 3H); 3.99(s, 3H); 4.58(q, 2H); 7.13(m, 2H); 7.26(m, 1H); 7.41(m, 2H); 8.42 (s, 1H); 9.69(s, 1H); 12.72(s, 1H); |
| 93 | (d₆ acetone)1.34(t, 3H); 2.51(s, 3H); 4.03(s, 3H); 4.58(q, 2H); 5.34 (s, 2H); 8.59(s, 1H); 9.65(s, 1H); 12.60(s, 1H); |
| 94 | 1.23(t, 3H); 3.89(s, 6H); 4.54(q, 2H); 5.97(s, 1H); 7.39(m, 2H); 8.29 m, 2H); 8.60(s, 1H); 10.65(s, 1H); 12.97(s, 1H); |
| 95 | 1.28(t, 3H); 2.41(s, 3H); 3.95(s, 3H); 4.55(q, 2H); 7.42(m, 2H); 8.31 (m, 2H); 8.60(s, 1H); 11.00(s, 1H); 12.67(s, 1H); |
| 96 | (d₆ acetone)1.35(t, 3H); 3.93(s, 6H); 4.61(q, 2H); 5.82(s, 1H); 7.31–7.62(m, 3H); 8.43(s, 1H); 9.5 (s, 1H); 13.0(s, 1H); |
| 97 | (d₆ acetone)1.40(t, 3H); 2.43(s, 3H); 4.00(s, 3H); 4.61(q, 2H), 7.33–7.62(m, 3H); 8.44(s, 1H); 9.7(s, 1H); 12.8(s, 1H); |
| 98 | (d₆ acetone)3.96(s, 6H); 5.38(s, 4H); 5.89(s, 1H); 8.69(s, 1H); 9.44 (s, 1H); 12.79(s, 1H); |
| 99 | (d₆ acetone)2.50(s, 3H); 4.02(s, 3H); 5.39(s, 4H); 8.68(s, 1H); 9.65(s, 1H); 12.56(s, 1H); |
| 101 | 2.45(s, 3H); 3.97(s, 3H); 5.31(t, 4H); 8.82(s, 1H); 11.08(s, 1H); 12.6(s, 1H); |
| 102 | (CDCl₃)3.95(s, 6H); 4.98(d, 4H); 5.14–5.40(m, 4H); 5.79(s, 1H); 5.85–6.00(m, 2H); 8.41(s, 1H); 12.67(s, 1H); |
| 103 | (CDCl₃)2.57(s, 3H); 4.05(s, 3H); 5.00(d, 4H); 5.16–5.44(m, 4H); 5.88–6.04(m, 2H); 7.59(br s 1H); 8.43(s, 1H); 12.39(s, 1H); |
| 104 | 3.47(t, 2H); 3.93(s, 6H); 5.13(d, 4H); 5.99(s, 1H); 8.73(s, 1H); 10.59(s, 1H); 13.0(s, 1H); |
| 105 | 2.48(s, 3H); 3.48(t, 2H); 3.99(s, 3H); 5.14(d, 4H); 8.73(s, 1H); 11.04(s, 1H); 12.7(s, 1H); |
| 108 | (d₆acetone)1.6(m, 6H); 3.97(s, 6H); 4.89–5.07(m, 4H); 5.60–5.88(m, 4H); 5.89(s, 1H); 8.51 (s, 1H); 9.30(s, 1H); 12.79 (s, 1H); |
| 109 | (d₆ acetone)1.6(m, 6H); 2.52(s, 3H); 4.04(s, 3H); 4.90–5.08(m, 4H); 5.60–5.9(m, 4H); 8.52(s, 1H); 10.19(s, 1H); 12.55(s, 1H); |
| 111 | 0.91(t, 3H); 1.65(m, 2H); 2.46(s, 3H); 3.98(s, 3H); 4.40(t, 2H); 4.97 (d, 2H); 5.12–5.40(m, 2H); 5.91(m, 1H); 8.61(s, 1H); 11.01(s, 1H); 12.50(s, 1H); |
| 112 | (d₆ acetone)3.91(s, 6H); 5.19(q, 2H); 5.76(s, 1H); 7.1–7.5(m, 5H); 8.50 (s, 1H); 10.19(s, 1H); 13.07(s, 1H); |
| 113 | (d₆ acetone)2.40(s, 3H); 3.98(s, 3H); 5.19(q, 2H); 7.1–7.5(m, 5H); 8.51 (s, 1H); 9.73(s, 1H); 12.86(s, 1H); |
| 115 | (d₆ acetone)1.03(t, 3H); 1.8(m, 2H); 2.41(s, 3H); 3.98(s, 3H); 4.50(t, 2H); 7.1–7.5(m, 5H); 8.41(s, 1H); 9.76(s, 1H); 12.8(s, 1H); |
| 107 | (d₆ acetone)2.29(s, 3H); 3,94(s, 3H); 7.15–7.20(m, 4H); 7.25–7.32 (m, 2H); 7.40–7.48(m, 4H); 8.34 (s, 1H); 9.76(s, 1H); |
| 117 | 1.33(t, 3H); 2.56(s, 3H); 4.08 (s, 3H); 4.58(q, 2H); 5.08(m, 2H); 5.25(m, 1H); 5.48(m, 1H); 6.05(m, 1H); 8.72(s, 1H); 11.2 (s, 1H); 12.6(s, 1H); |
| 118 | (CDCl₃)1.40(t, 3H); 3.97(s, 6H); 4.61(q, 2H); 5.81(s, 1H); 7.50(t, 1H); 8.47(s, 1H); 12.99 (s, 1H); |
| 119 | (CDCl₃)1.43(t, 3H); 2.58(s, 3H); 4.06(s, 3H); 4.61(q, 2H); 7.50(t, 1H); 8.48(s, 1H); 12.66 (s, 1H); |
| 120 | 2.5(s, 3H); 4.05(s, 3H); 5.0–5.5(m, 6H); 6.0(m, 1H); 8.8(s, 1H); 11.2(s, 1H) 12.8(s, 1H); |
| 121 | 1.35(t, 6H); 2.59(s, 3H); 3.45 (s, 3H); 4.08(s, 3H); 4.54(q, 4H); 8.41(s, 1H); 13.65(s, 1H); |
| 122 | 1.24(t, 3H); 2.52(s, 3H); 3.32(s, 3H); 4.02(s, 3H); 4.51(q, 2H); 5.18(q, 2H); 8.71(s, 1H); 13.96 (s, 1H); |

EXAMPLE 5

This non-limiting Example illustrates the preparation of formulations of the compounds of the invention.

a) Emulsifiable Concentrate

Compound No. 2 was dissolved in toluene/DMSO containing 7% v/v "Teric" N13 and 3% v/v "Kemmat" SC15B to give an emulsifiable concentrate which was diluted with water to the required concentration to give an aqueous emulsion which was applied by spraying. ("Teric" is a Trade Mark and "Teric" N13, is a product of ethoxylation of nonylphenol; "Kemmat" is a Trade Mark and "Kemmat" SC15B is a formulation of calcium dodecylbenzenesulfonate).

b) Aqueous Suspension

Compound No. 4 (5 parts by weight and "Dyapol" PT (1 part by weight) were added to a 2% aqueous solution (94 parts by weight) of "Teric" N8 and the mixture was ball milled to produce a stable aqueous suspension which may be diluted with water to the required concentration to give an aqueous suspension which may be applied by spraying.

("Dyapol" is a Trade Mark and "Dyapol" PT is an anionic suspending agent; "Teric" N8 is a product of ethoxylation of nonylphenol).

c) Emulsifiable Concentrate

Compound NO. 9 (10 parts by weight), "Teric" N13 (5 parts by weight) and "Kemmat" SC15B (5 parts by weight) were dissolved in "Solvesso" 150 (80 parts by weight) to give an emulsifiable concentrate which may be diluted with water to the required concentration to give an aqueous emulsion which may be applied by spraying. ("Solvesso" is a Trade Mark and "Solvesso" 150 is a high boiling point aromatic petroleum fraction).

d) Dispersible Powder

Compound No. 4 (10 parts by weight), "Matexil" DA/AC (3 parts by weight), "Aerosol" OT/B (1 part by weight) and china clay 298 (86 parts by weight) were blended and then milled to give a powder composition having a particle size below 50 microns.

("Matexil" is a Trade Mark and "Matexil" DA/AC is the disodium salt of a naphthalenesulfonic acid/formaldehyde condensate; "Aerosol" is a Trade Mark and "Aerosol" OT/B is a formulation of the dioctyl ester of sodium sulfosuccinic acid).

e) Dusting Powder

Compound No. 3 (10 parts by weight), attapulgite (10 parts by weight) and pyrophyllite (80 parts by weight) were thoroughly blended and then ground in a hammer-mill to produce a powder of particle size less than 200 microns.

Emulsifiable concentrates and/or suspensions of the compounds of the invention were prepared essentially as described in part a), b) or c) above and then diluted with water, optionally containing surface active agent and/or oil, to give aqueous compositions of the required concentration which were used, as described in Examples 6 and 7, in the evaluation of the pre-emergence and post-emergence herbicidal activity of the compounds.

EXAMPLE 6

The pre-emergent herbicidal activity of the compounds of the invention formulated as described in Example 5 was assessed by the following procedure:

The seeds of the test species were sown in rows 2 cm deep in soil contained in seed boxes. The monocotyledonous plants and the dicotyledonous plants were sown in separate boxes and after sowing the two boxes were sprayed with the required quantity of a composition of the invention. Two duplicate seed boxes were prepared in the same manner but were not sprayed with a composition of the invention and were not sprayed with a composition of the invention and were used for comparison purposes. All the boxes were placed in a glass house, lightly watered with an overhead spray to initiate germination and then sub-irrigated as required for optimum plant growth. After three weeks the boxes were removed from the glass house and the effect of the treatment was visually assessed. The results are presented in Table 3 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (-) means that no experiment was carried out.

The names of the test plants are as follows:

| | |
|---|---|
| Wh | Wheat |
| Ot | Wild Oats |
| Rg | Ryegrass |
| Jm | Japanese millet |
| B | Barley |
| P | Peas |
| Ip | Ipomea |
| Ms | Mustard |
| Sf | Sunflower |

TABLE 3

Pre-emergent Herbicidal Activity

| Compound No. | Application Rate kg/ha | Wh | Jm | Rg | Ot | B | Sf | Ip | Ms | P |
|---|---|---|---|---|---|---|---|---|---|---|
| 2 | 0.10 | 4 | 3 | 2 | 2 | 3 | 4 | 3 | 4 | 5 |
| 2 | 0.05 | 1 | 1 | 0 | 1 | 0 | 4 | 3 | 4 | 4 |
| 2 | 0.025 | 0 | 0 | 0 | 0 | 1 | 4 | 3 | 4 | 2 |
| 3 | 0.10 | 4 | 4 | 4 | 4 | 4 | 4 | 3 | 5 | 4 |
| 3 | 0.025 | 2 | 3 | 2 | 2 | 1 | 3 | 2 | 5 | 3 |
| 4 | 0.10 | 0 | 0 | 3 | 0 | 2 | 5 | 4 | 5 | 5 |
| 4 | 0.025 | 0 | 0 | 0 | 0 | 1 | 4 | 4 | 5 | 3 |
| 9 | 0.10 | 4 | 4 | 4 | 1 | 4 | 4 | 4 | 5 | 4 |
| 9 | 0.025 | 2 | 1 | 3 | 0 | 2 | 5 | 4 | 4 | 4 |
| 10 | 0.10 | — | — | — | — | — | 4 | 4 | 5 | 4 |
| 10 | 0.025 | — | — | — | — | — | 3 | 4 | 5 | 2 |
| 11 | 0.10 | 5 | 4 | 5 | 4 | 5 | 5 | 4 | 4 | 5 |
| 11 | 0.025 | 4 | 4 | 4 | 4 | 4 | 4 | 4 | 4 | 4 |
| 12 | 0.10 | 1 | 2 | 1 | 0 | 1 | 4 | 3 | 4 | 3 |
| 12 | 0.025 | 0 | 1 | 0 | 0 | 1 | 3 | 3 | 3 | 1 |
| 16 | 0.10 | 3 | 3 | 2 | 2 | 1 | 4 | 4 | 4 | 4 |
| 16 | 0.025 | 1 | 2 | 1 | 2 | 1 | 4 | 3 | 4 | 3 |
| 17 | 0.025 | — | — | — | — | — | 4 | 4 | 4 | 5 |
| 18 | 0.10 | 0 | 3 | 5 | 4 | 3 | 5 | 4 | 4 | 5 |
| 18 | 0.025 | 0 | 3 | 4 | 3 | 3 | 4 | 3 | 4 | 3 |
| 19 | 0.10 | 0 | 2 | 1 | 2 | 2 | 4 | 3 | 4 | 3 |
| 23 | 0.40 | 4 | 4 | 4 | 3 | 4 | 5 | 4 | 5 | 5 |
| 23 | 0.10 | — | — | — | — | — | 4 | 5 | 5 | 5 |
| 25 | 0.40 | 0 | 1 | 3 | 2 | 2 | 3 | 4 | 5 | 5 |
| 25 | 0.10 | 0 | 1 | 1 | 1 | 0 | 1 | 3 | 5 | 4 |
| 27 | 0.40 | 1 | 4 | 2 | 3 | 3 | 4 | 4 | 4 | 5 |
| 27 | 0.10 | 0 | 4 | 0 | 1 | 0 | 4 | 3 | 4 | 2 |
| 38 | 0.40 | 4 | 4 | 2 | 3 | 3 | 5 | 3 | 4 | 5 |
| 38 | 0.10 | 1 | 4 | 0 | 3 | 1 | 0 | 2 | 4 | 3 |
| 40 | 0.40 | 3 | 4 | 4 | 4 | 3 | 4 | 3 | 4 | 4 |
| 40 | 0.10 | 2 | 3 | 3 | 4 | 3 | 4 | 3 | 4 | 4 |
| 42 | 0.40 | 3 | 4 | 1 | 3 | 3 | 5 | 1 | 5 | 2 |
| 42 | 0.10 | — | — | — | — | — | 5 | 0 | 5 | 0 |
| 52 | 0.40 | 2 | 1 | 2 | 3 | 3 | 3 | 2 | 3 | 3 |
| 62 | 0.40 | 2 | 4 | 1 | 2 | 3 | 5 | 4 | 4 | 4 |
| 64 | 0.40 | 1 | 3 | 2 | 3 | 3 | 4 | 4 | 5 | 5 |
| 64 | 0.10 | 0 | 1 | 0 | 0 | 1 | 4 | 4 | 4 | 5 |
| 75 | 0.025 | 3 | 0 | 0 | 0 | 0 | 4 | 5 | 5 | 3 |

TABLE 3-continued

| | | Pre-emergent Herbicidal Activity | | | | | | | | |
|---|---|---|---|---|---|---|---|---|---|---|
| Compound No. | Application Rate kg/ha | TEST PLANTS | | | | | | | | |
| | | Wh | Jm | Rg | Ot | B | Sf | Ip | Ms | P |
| 76 | 0.025 | 1 | 1 | 1 | 0 | 1 | 4 | 2 | 3 | 3 |
| 77 | 0.10 | 3 | 0 | 1 | 0 | 0 | 4 | 5 | 5 | 4 |
| 78 | 0.40 | 1 | 4 | 4 | 1 | 0 | 4 | 4 | 5 | 3 |
| 79 | 0.025 | 1 | 3 | 3 | 3 | 3 | 4 | 4 | 4 | 4 |
| 81 | 0.025 | 1 | 0 | 3 | 3 | 2 | 4 | 4 | 4 | 4 |
| 83 | 0.40 | 4 | 4 | 4 | 4 | 4 | 4 | 3 | 5 | 5 |
| 84 | 0.40 | 0 | 3 | 0 | 2 | 0 | 4 | 4 | 5 | 4 |
| 85 | 0.025 | 0 | 2 | 2 | 2 | 0 | 5 | 3 | 4 | 5 |
| 87 | 0.025 | 0 | 3 | 2 | 3 | 3 | 4 | 3 | 3 | 3 |
| 88 | 0.10 | 0 | 0 | 0 | 0 | 0 | 4 | 2 | 4 | 3 |
| 89 | 0.10 | 0 | 0 | 4 | 2 | 2 | 4 | 4 | 4 | 5 |
| 90 | 0.025 | 2 | 0 | 0 | 2 | 3 | 4 | 3 | 3 | 3 |
| 91 | 0.025 | 0 | 1 | 1 | 1 | 0 | 4 | 3 | 4 | 2 |
| 93 | 0.40 | 0 | 4 | 4 | 3 | 0 | 5 | 3 | 4 | 3 |
| 99 | 0.10 | 3 | 3 | 1 | 2 | 0 | 4 | 5 | 5 | 4 |
| 101 | 0.10 | 0 | 0 | 1 | 0 | 0 | 4 | 3 | 3 | 3 |
| 102 | 0.025 | 0 | 0 | 0 | 0 | 0 | 4 | 4 | 3 | 3 |
| 103 | 0.025 | 0 | 0 | 0 | 0 | 0 | 4 | 4 | 3 | 5 |
| 104 | 0.025 | 0 | 0 | 0 | 0 | 0 | 4 | 4 | 5 | 4 |
| 105 | 0.40 | 0 | 0 | 3 | 0 | 2 | 4 | 3 | 4 | 4 |
| 107 | 0.40 | 2 | 3 | 4 | 3 | 3 | 5 | 4 | 4 | 5 |
| 109 | 0.40 | 0 | 0 | 0 | 0 | 0 | 4 | 3 | 4 | 2 |
| 111 | 0.10 | 0 | 2 | 3 | 3 | 1 | 4 | 4 | 4 | 5 |
| 112 | 0.40 | 1 | 4 | 4 | 0 | 0 | 4 | 3 | 4 | 4 |
| 113 | 0.10 | 1 | 0 | 4 | 3 | 1 | 4 | 3 | 5 | 4 |
| 115 | 0.40 | 2 | 1 | 3 | 3 | 1 | 5 | 4 | — | 5 |
| 117 | 0.40 | 0 | 2 | 4 | 3 | 1 | 5 | 4 | — | 5 |
| 121 | 0.40 | 1 | 3 | 1 | 3 | 0 | 1 | 5 | 5 | 4 |
| 122 | 0.40 | 0 | 3 | 3 | 0 | 0 | 3 | 2 | 2 | 2 |
| Comparative Compound No 3.21 from European Patent 96,004 | 0.40 | 0 | 0 | 0 | 0 | 0 | 0 | 0 | 0 | 0 |
| | 0.10 | 0 | 0 | 0 | 0 | 0 | 0 | 0 | 0 | 0 |

EXAMPLE 7

The post-emergent herbicidal activity of the compounds of the invention formulated as described in Example 5 was assessed by the following procedure.

The seeds of the test species were sown in rows 2 cm deep in soil contained in seed boxes. The monocotyledonous plants and the dicotyledonous plants were sown in separate seed boxes in duplicate. The four seed boxes were placed in a glass house, lightly watered with an overhead spray to initiate germination and then sub-irrigated as required for optimum plant growth. After the plants had grown to a height of about 10 to 12.5 cm one box of each of the monocotyledonous plants and the dicotyledonous plants was removed from the glass house and sprayed with the required quantity of a composition of the invention. After spraying the boxes were returned to the glass house for a further 3 weeks and the effect of treatment was visually assessed by comparison with the untreated controls. The results are presented in Table 4 where the damage to plants is rated on a scale of from 0 to 5 where 0 represents from 0 to 10% damage, 1 represents from 11 to 30% damage, 2 represents from 31 to 60% damage, 3 represents from 61 to 80%. damage, 4 represents from 81 to 90%. damage and 5 represents 100% kill. A dash (-) means that no experiment was carried out.

The names of the test plants are as follows:

| | |
|---|---|
| Wh | Wheat |
| Ot | Wild Oats |
| Rg | Ryegrass |
| Jm | Japanese millet |
| B | Barley |
| P | Peas |
| Ip | Ipomea |
| Ms | Mustard |
| Sf | Sunflower |
| Mz | Maize |

TABLE 4

| | | Post-emergent Herbicidal Activity | | | | | | | | | |
|---|---|---|---|---|---|---|---|---|---|---|---|
| Compound No. | Application Rate kg/ha | TEST PLANTS | | | | | | | | | |
| | | Wh | Jm | Rg | Ot | B | Sf | Ip | Ms | P | Mz |
| 2 | 0.10 | 1 | 2 | 0 | 0 | 1 | 5 | 5 | 5 | 4 | 4 |
| 2 | 0.025 | 0 | 0 | 0 | 0 | 0 | 4 | 5 | 5 | 3 | 2 |
| 3 | 0.10 | 3 | 2 | 3 | 2 | 3 | 5 | 3 | 5 | 5 | 4 |
| 3 | 0.025 | 2 | 1 | 1 | 1 | 2 | 5 | 2 | 4 | 3 | 4 |
| 4 | 0.10 | 0 | 0 | 3 | 1 | 1 | 5 | 4 | 5 | 5 | 2 |
| 4 | 0.025 | 0 | 0 | 1 | 1 | 1 | 5 | 4 | 5 | 4 | 0 |
| 9 | 0.10 | 0 | 3 | 4 | 0 | 1 | 5 | 4 | 5 | 5 | 5 |
| 9 | 0.025 | 0 | 1 | 2 | 0 | 0 | 3 | 3 | 5 | 5 | 4 |
| 10 | 0.10 | 2 | 0 | 4 | 4 | 2 | 5 | 4 | 5 | 4 | 5 |
| 10 | 0.025 | 0 | 0 | 0 | 3 | 0 | 4 | 3 | 4 | 2 | 4 |
| 11 | 0.10 | 3 | 4 | 5 | 3 | 4 | 5 | 4 | 5 | 4 | 3 |
| 11 | 0.025 | 3 | 4 | 5 | 3 | 3 | 5 | 3 | 4 | 3 | 3 |
| 12 | 0.10 | 1 | 5 | 3 | 1 | 0 | 5 | 4 | 5 | 3 | 3 |
| 12 | 0.025 | 0 | 4 | 0 | 1 | 0 | 5 | 3 | 5 | 3 | 2 |
| 16 | 0.10 | 3 | 4 | 1 | 2 | 2 | 5 | 5 | 5 | 4 | 4 |
| 16 | 0.025 | 3 | 2 | 0 | 0 | 2 | 5 | 4 | 5 | 4 | 3 |
| 17 | 0.10 | 3 | 0 | 2 | 3 | 2 | 5 | 4 | 5 | 5 | 5 |
| 17 | 0.025 | 0 | 0 | 0 | 2 | 0 | 5 | 3 | 4 | 4 | 5 |
| 18 | 0.10 | 0 | 3 | 3 | 1 | 2 | 5 | 5 | 5 | 4 | 3 |
| 18 | 0.025 | 0 | 2 | 1 | 1 | 2 | 5 | 4 | 4 | 5 | 1 |
| 19 | 0.10 | 1 | 3 | 1 | 2 | 1 | 5 | 4 | 5 | 3 | 3 |
| 19 | 0.025 | 1 | 2 | 0 | 1 | 0 | 5 | 3 | 4 | 1 | 2 |
| 23 | 0.10 | 3 | 1 | 0 | 1 | 1 | 4 | 3 | 4 | 3 | 4 |
| 23 | 0.025 | 1 | 0 | 0 | 0 | 0 | 4 | 3 | 4 | 2 | — |
| 25 | 0.40 | 0 | 0 | 3 | 3 | 0 | 4 | 4 | 5 | 3 | 4 |
| 27 | 0.40 | 0 | 3 | 1 | 0 | 2 | 5 | 4 | 5 | 3 | 4 |
| 27 | 0.10 | 0 | 3 | 0 | 0 | 1 | 5 | 3 | 5 | 2 | 4 |
| 38 | 0.10 | 1 | 3 | 0 | 2 | 2 | 5 | 5 | 5 | 3 | 4 |

TABLE 4-continued

Post-emergent Herbicidal Activity

| Compound No. | Application Rate kg/ha | TEST PLANTS | | | | | | | | | |
|---|---|---|---|---|---|---|---|---|---|---|---|
| | | Wh | Jm | Rg | Ot | B | Sf | Ip | Ms | P | Mz |
| 38 | 0.025 | 3 | 3 | 0 | 1 | 2 | 4 | 4 | 4 | 3 | 3 |
| 40 | 0.10 | 2 | 1 | 1 | 3 | 3 | 5 | 4 | 4 | 3 | 4 |
| 40 | 0.025 | 0 | 0 | 3 | 2 | 4 | 3 | 3 | 3 | 4 | |
| 42 | 0.40 | 3 | 4 | 0 | 2 | 4 | 5 | 4 | 5 | 3 | 4 |
| 42 | 0.10 | — | — | — | — | — | 5 | 4 | 4 | 2 | — |
| 44 | 0.40 | 1 | 4 | 4 | 3 | 4 | 5 | 3 | 4 | 4 | 4 |
| 52 | 0.40 | 0 | 0 | 0 | 2 | 2 | 5 | 3 | 4 | 3 | 4 |
| 62 | 0.025 | 1 | 3 | 0 | 0 | 1 | 5 | 5 | 5 | 0 | 3 |
| 64 | 0.40 | 0 | 5 | 2 | 3 | 3 | 5 | 5 | 5 | 5 | 4 |
| 64 | 0.10 | 0 | 3 | 0 | 2 | 3 | 5 | 5 | 5 | 5 | 4 |
| 75 | 0.40 | 0 | 3 | 3 | 2 | 3 | 5 | 5 | 5 | 4 | 5 |
| 76 | 0.10 | 1 | 3 | 3 | 2 | 3 | 5 | 5 | 5 | 3 | 4 |
| 76 | 0.025 | 0 | 1 | 1 | 1 | 0 | 5 | 5 | 5 | 3 | 4 |
| 77 | 0.40 | 0 | 4 | 4 | 3 | 2 | 5 | 4 | 5 | 3 | 5 |
| 77 | 0.10 | 0 | 3 | 3 | 1 | 2 | 4 | 5 | 5 | 3 | 4 |
| 78 | 0.40 | 3 | 2 | 1 | 1 | 3 | 5 | 4 | 5 | 4 | 4 |
| 79 | 0.10 | 2 | 4 | 4 | 3 | 3 | 5 | 4 | 4 | 4 | 4 |
| 80 | 0.40 | 3 | 4 | 2 | 0 | 3 | 4 | 2 | 5 | 3 | 3 |
| 81 | 0.025 | 2 | 0 | 3 | 3 | 3 | 5 | 4 | 3 | 3 | 2 |
| 83 | 0.10 | 4 | 4 | 4 | 4 | 4 | 5 | 5 | 5 | 4 | 3 |
| 84 | 0.40 | 4 | 4 | 4 | 3 | 3 | 5 | 5 | 5 | 4 | 4 |
| 84 | 0.025 | 2 | 3 | 1 | 0 | 1 | 5 | 4 | 5 | 3 | 3 |
| 85 | 0.40 | 1 | 5 | 4 | 3 | 1 | 5 | 4 | — | 5 | 4 |
| 85 | 0.10 | 1 | 4 | 4 | 2 | 1 | 5 | 4 | 5 | 4 | 3 |
| 87 | 0.40 | 1 | 4 | 3 | 3 | 4 | 5 | 4 | 5 | 4 | 3 |
| 87 | 0.025 | 0 | 3 | 0 | 0 | 2 | 5 | 4 | 4 | 3 | 0 |
| 88 | 0.40 | 1 | 3 | 0 | 0 | 3 | 4 | 4 | 5 | 4 | 2 |
| 88 | 0.025 | 0 | 0 | 0 | 0 | 2 | 4 | 3 | 3 | 2 | 0 |
| 89 | 0.40 | 1 | 0 | 2 | 1 | 3 | 5 | 4 | 4 | 3 | 3 |
| 89 | 0.025 | 0 | 0 | 0 | 0 | 0 | 5 | 3 | 3 | 2 | 0 |
| 90 | 0.40 | 3 | 4 | 4 | 3 | 4 | 5 | 5 | 5 | 4 | 4 |
| 90 | 0.025 | 1 | 3 | 0 | 2 | 2 | 4 | 4 | 5 | 4 | 2 |
| 91 | 0.10 | 0 | 2 | 4 | 2 | 2 | 5 | 5 | 5 | 3 | 2 |
| 91 | 0.025 | 0 | 0 | 3 | 1 | 0 | 4 | 3 | 5 | 2 | 0 |
| 93 | 0.40 | 0 | 5 | 4 | 3 | 3 | 5 | 4 | 5 | 4 | 3 |
| 93 | 0.01 | 0 | 4 | 3 | 2 | 1 | 5 | 4 | 4 | 4 | 1 |
| 94 | 0.40 | 2 | 1 | 1 | 0 | 1 | 4 | 4 | 3 | 3 | 3 |
| 95 | 0.40 | 0 | 1 | 1 | 0 | 1 | 2 | 1 | 4 | 2 | 0 |
| 96 | 0.40 | 0 | 1 | 1 | 0 | 0 | 3 | 3 | 3 | 3 | 1 |
| 97 | 0.40 | 2 | 4 | 2 | 1 | 2 | 5 | 4 | 4 | 3 | 2 |
| 98 | 0.40 | 1 | 0 | 2 | 0 | 3 | 4 | 4 | 5 | 3 | 0 |
| 99 | 0.40 | 0 | 3 | 2 | 1 | 1 | 4 | 4 | 3 | 3 | 3 |
| 101 | 0.40 | 1 | 3 | 3 | 1 | 1 | 4 | 4 | 5 | 3 | 3 |
| 102 | 0.10 | 2 | 1 | 0 | 0 | 3 | 5 | 4 | 5 | 3 | 3 |
| 102 | 0.025 | 1 | 0 | 0 | 0 | 1 | 4 | 4 | 5 | 2 | 2 |
| 103 | 040 | 2 | 3 | 3 | 2 | 3 | 5 | 5 | 5 | 5 | 4 |
| 103 | 0.10 | 0 | 0 | 3 | 0 | 2 | 5 | 5 | 5 | 5 | 3 |
| 103 | 0.025 | 1 | 0 | 2 | 0 | 1 | 5 | 4 | 5 | 5 | 0 |
| 104 | 0.10 | 1 | 3 | 0 | 0 | 1 | 4 | 3 | 5 | 3 | 0 |
| 105 | 0.40 | 1 | 1 | 2 | 1 | 2 | 4 | 3 | 5 | 3 | 4 |
| 106 | 0.40 | 0 | 0 | 1 | 0 | 1 | 4 | 2 | 4 | 2 | 1 |
| 107 | 0.40 | 0 | 1 | 3 | 3 | 2 | 4 | 3 | — | 4 | 3 |
| 108 | 0.40 | 0 | 1 | 1 | 0 | 0 | 3 | 2 | 5 | 3 | 1 |
| 109 | 0.40 | 0 | 0 | 0 | 0 | 0 | 5 | 3 | 5 | 4 | 1 |
| 111 | 0.10 | 1 | 2 | 4 | 2 | 2 | 5 | 5 | 5 | 4 | 3 |
| 111 | 0.025 | 0 | 1 | 2 | 1 | 1 | 5 | 3 | 5 | 3 | 0 |
| 112 | 0.10 | 0 | 1 | 1 | 0 | 0 | 5 | 3 | 5 | 3 | 1 |
| 112 | 0.025 | 0 | 0 | 0 | 0 | 0 | 5 | 3 | 5 | 3 | 0 |
| 113 | 0.10 | 1 | 3 | 3 | 1 | 1 | 5 | 3 | 4 | 3 | 3 |
| 113 | 0.025 | 0 | 0 | 1 | 0 | 0 | 5 | 2 | 3 | 2 | 1 |
| 115 | 0.10 | 0 | 1 | 4 | 1 | 0 | 5 | 4 | 4 | 4 | 2 |
| 115 | 0.025 | 0 | 1 | 1 | 0 | 0 | 4 | 4 | 4 | 3 | 0 |
| 117 | 0.10 | 0 | 0 | 4 | 0 | 0 | 5 | 4 | — | 5 | 2 |
| 117 | 0.025 | 0 | 0 | 2 | 0 | 0 | 5 | 3 | — | 3 | 0 |
| 121 | 0.40 | 0 | 2 | 2 | 2 | 0 | 3 | 3 | 3 | 2 | 3 |
| 122 | 0.40 | 0 | 1 | 0 | 1 | 1 | 4 | 4 | 4 | 3 | 1 |
| Comparative Compound No 3.21 from European Patent Appl 96,004 | 0.40 | 0 | 0 | 0 | 0 | 0 | 1 | 0 | 1 | 0 | 0 |
| | 0.10 | 0 | 0 | 0 | 0 | 0 | 0 | 0 | 0 | 0 | 0 |

What we claim is as follows:

1. A compound of formula I and salts thereof

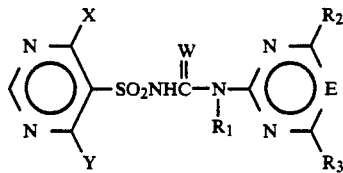

wherein:
X and Y are independently selected from ethoxy, propoxy, isopropoxy, n-butoxy, difluoromethoxy, 2,2,2-trifluoroethoxy, 2,2,2-trichloroethoxy, allyloxy and propargyloxy; W is oxygen; E is nitrogen; $R_1$ is hydrogen; $R_2$ and $R_3$ are independently selected from methyl, methoxy, chloro or difluoromethoxy.

2. A compound according to claim 1 wherein:
X and Y are independently selected from ethoxy, propoxy, isopropoxy, difluoromethoxy, trilfluoro ethoxy, and allyloxy;
W is oxygen;
E is nitrogen;
$R_1$ is hydrogen;
$R_2$ and $R_3$ are independently selected from methyl, methoxy and chloro.

3. A herbicidal composition comprising as active ingredient a compound of formula I as defined according to claim 1 and a carrier therefor.

4. A process for severely damaging or killing unwanted plants which process comprises applying to the plants, or to the growth medium of the plants, an effective amount of a compound according to claim 1.

5. A process for controlling weeds in cultivated crops which process comprises applying to the crop, or to the growth medium of the crop, a compound according to claim 1, in an amount sufficient to severely damage or kill the weeds but insufficient to damage the crop substantially.

6. A process for regulating the growth of a plant which process comprises applying to the plant, to the seed of the plant, or to the growth medium of the plant, an effective amount of a compound according to claim 1.

7. A plant growth regulating composition comprising as active ingredient a compound as defined according to claim 1 and an inert carrier therefor.